United States Patent [19]
Furuya et al.

[11] Patent Number: 6,004,954
[45] Date of Patent: Dec. 21, 1999

[54] CONDENSED THIAZINE DERIVATIVES, THEIR PRODUCTION AND USE THEREOF

[75] Inventors: Shuichi Furuya, Ibaraki; Seiichi Tanida, Kyoto; Yoshikazu Ohta, Osaka, all of Japan

[73] Assignee: Takeda Chemical Industries, Ltd., Osaka, Japan

[21] Appl. No.: 08/813,986

[22] Filed: Mar. 10, 1997

[30] Foreign Application Priority Data

Mar. 13, 1996 [JP] Japan ................................ 8-055809

[51] Int. Cl.$^6$ ................... A61K 31/54; C07D 513/04
[52] U.S. Cl. .................................. 514/224.2; 544/48
[58] Field of Search ............................ 544/48; 514/224.2

[56] References Cited

U.S. PATENT DOCUMENTS

4,315,767  2/1982  Wolf ............................................ 71/91

FOREIGN PATENT DOCUMENTS

2-275869  11/1990  Japan .
2-275870  11/1990  Japan .

OTHER PUBLICATIONS

Lafaille, "The Role of Helper T Cell Subsets in Autoimmune Diseases," Cytokine & Growth Factor Reviews, vol. 9, No. 2, pp. 139–151, Jun. 1998.

Ead et al., "Synthesis and Reactions of New 1,2,4–Triazoles and Their Biological Activities," Arch. Pharm., vol. 323, No. 1, pp. 57–58, 1990.

C.V. Reddy Sastry et al., "An improved synthesis of 2,4–dihydro–1–oxo–1,2,4]triazolo[3,4–c][1,4]–benzoxazines and –benzothiazines", Chemistry and Industry, 3, pp. 227–228, 1989.

D. Spinelli et al., "A new ring transformation: conversion of 6–p–chlorophenyl–3–methyl–5–nitrosoimidazo[2,1–b]thiazole into 8–p–chlorophenyl–8–hydroxy–5–methyl–3–oxo–1,2,4–oxadiazolo[3,4–c][1,4–]thiazine by the action of mineral acids", J. Chem. Soc. Chem. Commun., 19, pp. 1394–1395, 1992.

R. Mitra et al., "Synthesis of 1,2,4–triazolo fused heterocycels", Heterocycles, vol. 27, No. 10, pp. 2297–2300, 1988.

S.S. Tandon et al., "A structual reassignment: 5,8a–Diphenyl–2,3,8,8a–tetrahydro–1H–imidazo[2,1–c][1,4]thiazine", Synthesis, 6, pp. 481–482, 1983.

CAS online abstract of Khim. Geterotsikl., Soedin., 9, pp. 1211–20, 1979.

Primary Examiner—Mukund J. Shah
Assistant Examiner—Ann M. Kessinger
Attorney, Agent, or Firm—Wenderoth, Lind & Ponack L.L.P.

[57] ABSTRACT

This invention relates to a compound of the following formula or a salt thereof, their production and use.

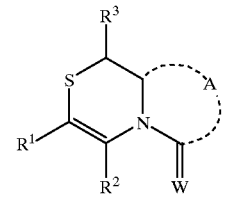

[I]

wherein $R^1$ and $R^2$ independently represent hydrogen, a group bonding through a carbon atom, a group bonding through a nitrogen atom, a group bonding through an oxygen atom, or a group bonding through a sulfur atom; $R^3$ represents hydrogen, halogen, a group bonding through a carbon atom, a group bonding through a nitrogen atom, a group bonding through an oxygen atom, or a group bonding through a sulfur atom; W represents an oxygen atom or sulfur atom; A represents a group forming a nitrogen-containing condensed ring at the 3,4- of a 1,4-thiazine ring; $R^1$ and $R^2$ may be combined to form a bivalent hydrocarbon group interrupted by one or more hetero atoms or an alkylene group. The above compound or a salt thereof not only has Th1 and Th2 cell function modulating activity but has splenocyte proliferation response, interleukin-5 production, and interferon-gamma production inhibitory activity and finds application as an effective therapeutic and/or prophylactic agent for allergic or autoimmune diseases or as an effective therapeutic and/or prophylactic agent for graft rejection or graft-vs-host disease.

6 Claims, No Drawings

CONDENSED THIAZINE DERIVATIVES, THEIR PRODUCTION AND USE THEREOF

FIELD OF THE INVENTION

The present invention relates to a condensed thiazine derivative useful as a therapeutic or prophylactic drug for diseases resulting from abnormalities of the immune mechanism, diseases accompanied by abnormalities of the immune mechanism, and graft rejection or graft-vs-host diseases associated with organ or bone marrow transplantation and to a method for production of the derivative.

BACKGROUND OF THE INVENTION

In allergic, autoimmune and other diseases associated with abnormalities of the immunological function, and diseases accompanied by abnormalities of the function, a derangement of the balance of T cell subsets is frequently found and it is being made increasingly clear that this derangement has much to do with the onset and exacerbation of those diseases [Annual Review of Immunology, 12, 227–257 (1994); Trends in Pharmacological Science, 15, 324–332 (1994), Immunology Today, 16, 34–38 (1995), ditto, 17, 138–146 (1996)]. However, there is not known a therapeutic drug that exhibits efficacy in such diseases through positive correction of the balance of T cell subsets.

Meanwhile, in the field of organ transplantation, it is known that T helper-1 cells play a central role in graft rejection. However, there is not known a drug that would contribute to an increased survival of grafts or prevent graft-vs.-host diseases due to transplanted myelocytes by selective modulation of the functions of T cell subsets.

A monocyclic 1,4-thiazine compound having antiallergic activity is disclosed in JP-A 275869/1990. A tricyclic 1,4-thiazine derivative having antiallergic activity is described in Chemical and Industry, 3, 227–228 (1989). JP-A 275870/1990 describes an antiallergic bicyclic 1,4-thiazine derivative.

Aside from them, several other bicyclic 1,4-thiazine derivatives are described in Journal of Chemical Society Chemistry Communication, 19, 1394–1395 (1992), Heterocycles, 27(10), 2297–2300 (1988), and Synthesis, 6, 481–482 (1983).

Recent years have seen an increased incidence of allergic, autoimmune, and other diseases associated with immunological abnormalities, and diseases accompanied by such immunological abnormalities and this is presenting a serious problem in medical care today. This category of illness encompasses a broad spectrum of diseases such as rheumatoid arthritis, systemic lupus erythematosus, multiple sclerosis, malignant anemia, ideopathic thrombocytopenic purpura, severe myasthenia, scleroderma, uveitis, Hashimoto's disease, Sjögren's disease, Addison's disease, Basedow's disease, granulocytopenia, bronchial asthma, allergic rhinitis, atopic dermatitis, pollinosis, contact dermatitis, hypersensitivity pneumonitis, lupus nephritis, inflammatory bowel disease, chronic obstructive pulmonary disease, and psoriasis, among others. Recently, the abnormality of the balance of T cell subsets as found in these diseases has gathered attention and, in particular, it is conjectured today that a marked bias in favor of T helper-1 cells or helper-2 cells is a major factor in the onset and exacerbation of such diseases. For the treatment of these diseases, a variety of drugs including steroids, nonsteroidal antiinflammatory drugs, and antihistaminics have been employed but no satisfactory efficacy has been obtained to this day.

Moreover, in the field of organ transplantation, it is known, as mentioned above, that T helper-1 cells play a cardinal role in graft rejection. In this field, steroids, cytotoxic agents, cyclosporins, and tacrolimus, among others, are being used for increasing the survival of grafts or preventing graft-vs-host diseases due to transplanted myelocytes but the adverse reactions associated with the use of these drugs, such as renal impairment and liver damage, are presenting problems today.

SUMMARY OF THE INVENTION

In view of the above state of the art, the present inventors giving thought to the above-mentioned derangement of the balance of T cell subsets in said diseases, explored compounds having immunomodulating activity from this new point of view. As a result, they discovered that a condensed 1,4-thiazine derivative having a moiety of the following partial formula:

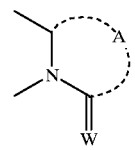

bonded at the 3,4-positions of the thiazine nucleus efficiently suppresses the antigen-specific proliferation of murine splenocytes of mice sensitized with ascaris antigen or purified protein derivative (briefly, PPD) and, after further research based on this finding, have perfected the present invention.

The present invention, therefore, relates to (1) A compound of the formula:

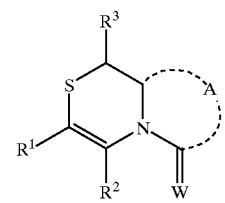

[I]

wherein $R^1$ and $R^2$ independently represent hydrogen, a group bonding through a carbon atom, a group bonding through a nitrogen atom, a group bonding through an oxygen atom, or a group bonding through a sulfur atom; $R^3$ represents hydrogen, halogen, a group bonding through a carbon atom, a group bonding through a nitrogen atom, a group bonding through an oxygen atom, or a group bonding through a sulfur atom; W represents an oxygen atom or a sulfur atom; A represents a group forming a nitrogen-containing condensed ring at the 3,4-position of a 1,4-thiazine ring; $R^1$ and $R^2$ may be combined to form a bivalent hydrocarbon group interrupted by one or more hetero atoms or an alkylene group; or a salt thereof, (2) the compound as described in (1), wherein the moiety represented by the partial structural formula:

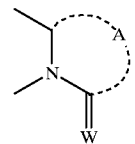

is a 5- or 6-membered cyclic group which contains 1 to 3 nitrogen atoms and which is substituted with oxo or thioxo, (3) the compound as described in (1), wherein the moiety represented by the partial structural formula:

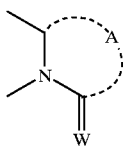

is a group of the formula:

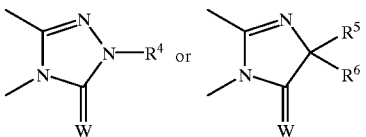

wherein $R^4$ represents hydrogen, a group bonding through a carbon atom or a group bonding through a sulfur atom; $R^5$ and $R^6$ independently represent hydrogen, a group bonding through a carbon atom, a group bonding through a nitrogen atom, a group bonding through an oxygen atom, or a group bonding through a sulfur atom; W has the same meaning as defined in (1), (4) the compound as described in (1), wherein the compound of the formula is represented by the formula:

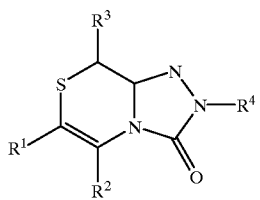

[II]

wherein $R^1$, $R^2$, and $R^3$ have the same meanings as defined in (1); $R^4$ has the same meaning as defined in (3), (5) the compound as described in (1), wherein $R^1$ represents (1) hydrogen, (2) a $C_{1-15}$ alkyl group which may optionally be substituted with (i) a $C_{3-7}$ cycloalkyl group, (ii) a $C_{3-10}$ cycloalkenyl group, (iii) nitro, (iv) hydroxy, (v) mercapto, (vi) oxo, (vii) thioxo, (viii) cyano, (ix) carbamoyl, (x) carboxy, (xi) a $C_{1-6}$ alkoxy-carbonyl group, (xii) sulfo, (xiii) halogen, (xiv) a $C_{1-6}$ alkoxy group, (xv) a $C_{6-20}$ aryloxy group, (xvi) a $C_{1-6}$ acyloxy group, (xvii) a $C_{1-6}$ alkylthio group, (xviii) a $C_{6-10}$ arylthio group, (xix) a $C_{1-6}$ alkylsulfinyl group, (xx) a $C_{6-10}$ arylsulfinyl group, (xxi) a $C_{1-6}$ alkylsulfonyl group, (xxii) a $C_{6-10}$ arylsulfonyl group, (xxiii) amino, (xxiv) a $C_{1-6}$ acylamino group, (xxv) a mono- or di-$C_{1-6}$ alkylamino group, (xxvi) a $C_{3-8}$ cycloalkylamino group, (xxvii) a $C_{6-14}$ arylamino group, (xxviii) a $C_{1-6}$ alkyl-carbonyl group, (xxix) a $C_{1-6}$ alkyl-carbonyloxy group, (xxx) a $C_{6-10}$ aryl-carbonyl group, or (xxxi) a heterocyclic group, (3) a $C_{6-14}$ aryl group which may optionally be substituted with (i) a $C_{1-15}$ alkyl group which may optionally be substituted with halogen, (ii) a $C_{3-7}$ cycloalkyl group, (iii) a $C_{2-10}$ alkenyl group, (iv) a $C_{2-10}$ alkinyl group, (v) a $C_{3-10}$ cycloalkenyl group, (vi) a $C_{6-14}$ aryl group, (vii) a $C_{7-15}$ aralkyl group, (viii) nitro, (ix) hydroxy, (x) mercapto, (xi) oxo, (xii) thioxo, (xiii) cyano, (xiv) carbamoyl, (xv) carboxy, (xvi) a $C_{1-6}$ alkoxy-carbonyl group, (xvii) sulfo, (xviii) halogen, (xix) a $C_{1-6}$ alkoxy group, (xx) a $C_{6-20}$ aryloxy group, (xxi) a $C_{7-20}$ aralkyloxy group, (xxii) a $C_{1-6}$ acyloxy group, (xxiii) a $C_{1-6}$ alkylthio group, (xxiv) a $C_{6-10}$ arylthio group, (xxv) a $C_{1-6}$ alkylsulfinyl group, (xxvi) a $C_{6-10}$ arylsulfinyl group, (xxvii) a $C_{1-6}$ alkylsulfonyl group, (xxviii) a $C_{6-10}$ arylsulfonyl group, (xxix) amino, (xxx) a $C_{1-6}$ acylamino group, (xxxi) a mono- or di-$C_{1-6}$ alkylamino group, (xxxii) a $C_{3-8}$ cycloalkylamino group, (xxxiii) a $C_{6-14}$ arylamino group, (xxxiv) a $C_{1-6}$ alkyl-carbonyl group, (xxxv) a $C_{1-6}$ alkyl-carbonyloxy group, (xxxvi) a $C_{6-10}$ aryl-carbonyl group, or (xxxvii) a heterocyclic group, (4) a $C_{1-15}$ acyl group, (5) a carbamoyl group, (6) a group of the formula —$NR^{100}R^{101}$, wherein $R^{100}$ and $R^{101}$ independently represent hydrogen, an optionally substituted $C_{1-15}$ alkyl group, or an optionally substituted $C_{6-14}$ aryl group, or (7) a heterocyclic group, (6) the compound as described in (1), wherein $R^2$ represents (1) hydrogen, (2) a $C_{1-15}$ alkyl group which may optionally be substituted with (i) a $C_{3-7}$ cycloalkyl group, (ii) a C3–10 cycloalkenyl group, (iii) nitro, (iv) hydroxy, (v) mercapto, (vi) oxo, (vii) thioxo, (viii) cyano, (ix) carbamoyl, (x) carboxy, (xi) a $C_{1-6}$ alkoxy-carbonyl group, (xii) sulfo, (xiii) halogen, (xiv) a $C_{1-6}$ alkoxy group, (xv) a $C_{6-20}$ aryloxy group, (xvi) a $C_{1-6}$ acyloxy group, (xvii) a $C_{1-6}$ alkylthio group, (xviii) a $C_{6-10}$ arylthio group, (xix) a $C_{1-6}$ alkylsulfinyl group, (xx) a $C_{6-10}$ arylsulfinyl group, (xxi) a $C_{1-6}$ alkylsulfonyl group, (xxii) a $C_{6-10}$ arylsulfonyl group, (xxiii) amino, (xxiv) a $C_{1-6}$ acylamino group, (xxv) a mono- or di-$C_{1-6}$ alkylamino group, (xxvi) a $C_{3-8}$ cycloalkylamino group, (xxvii) a $C_{6-14}$ arylamino group, (xxviii) a $C_{1-6}$ alkyl-carbonyl group, (xxix) a $C_{1-6}$ alkyl-carbonyloxy group, (xxx) a $C_{6-10}$ aryl-carbonyl group, or (xxxi) a heterocyclic group, (3) a $C_{6-14}$ aryl group which may optionally be substituted with (i) a $C_{1-15}$ alkyl group which may optionally be substituted with halogen, (ii) a $C_{3-7}$ cycloalkyl group, (iii) a $C_{2-10}$ alkenyl group, (iv) a $C_{2-10}$ alkinyl group, (v) a $C_{3-10}$ cycloalkenyl group, (vi) a $C_{6-14}$ aryl group, (vii) a $C_{7-15}$ aralkyl group, (viii) nitro, (ix) hydroxy, (x) mercapto, (xi) oxo, (xii) thioxo, (xiii) cyano, (xiv) carbamoyl, (xv) carboxy, (xvi) a $C_{1-6}$ alkoxy-carbonyl group, (xvii) sulfo, (xviii) halogen, (xix) a $C_{1-6}$ alkoxy group which may optionally be substituted with (a) a group of the formula —$CONR^{21}R^{22}$, wherein $R^{21}$ and $R^{22}$ independently represent hydrogen, a $C_{1-6}$ alkyl group, a $C_{1-6}$ alkoxy group, a $C_{3-7}$ cycloalkyl group, a $C_{6-14}$ aryl group or a $C_{7-20}$ aralkyl group, or (b) a heterocyclic group, (xx) an optionally substituted $C_{6-20}$ aryloxy group, (xxi) an optionally substituted $C_{7-20}$ aralkyloxy group, (xxii) a $C_{1-6}$ acyloxy group, (xxiii) a $C_{1-6}$ alkylthio group, (xxiv) a $C_{6-10}$ arylthio group, (xxv) a $C_{1-6}$ alkylsulfinyl group, (xxvi) a $C_{6-10}$ arylsulfinyl group, (xxvii) a $C_{1-6}$ alkylsulfonyl group, (xxviii) a $C_{6-10}$ arylsulfonyl group, (xxix) amino, (xxx) a $C_{1-6}$ acylamino group, (xxxi) a mono- or di-$C_{1-6}$ alkylamino group, (xxxii) a $C_{3-8}$ cycloalkylamino group, (xxxiii) a $C_{6-14}$ arylamino group, (xxiv) a $C_{1-6}$ alkyl-carbonyl group, (xxxv) a $C_{1-6}$ alkyl-carbonyloxy group, (xxxvi) a $C_{6-10}$ aryl-carbonyl group, or (xxxvii) a heterocyclic group, (4) a group of the formula —$COOR^{102}$, wherein $R^{102}$ represents hydrogen or a $C_{1-15}$ alkyl group, or (5) a heterocyclic group which may optionally be substituted with $C_{1-15}$ alkyl, (7) the compound as described in (1), wherein $R^3$ represents (1) hydrogen, (2) a $C_{1-15}$ alkyl group which may optionally be substituted with (i) a $C_{3-7}$ cycloalkyl group, (ii) a $C_{3-10}$ cycloalkenyl group, (iii) nitro, (iv) hydroxy, (v) mercapto, (vi) oxo, (vii) thioxo, (viii) cyano, (ix) carbamoyl, (x) carboxy, (xi) a $C_{1-6}$ alkoxy-carbonyl group, (xii) sulfo, (xiii) halogen, (xiv) a $C_{1-6}$ alkoxy group, (xv) a $C_{6-20}$ aryloxy group, (xvi) a $C_{1-6}$ acyloxy group, (xvii) a $C_{1-6}$ alkylthio group, (xviii) a $C_{6-10}$ arylthio group, (xix) a $C_{1-6}$ alkylsulfinyl group, (xx) a $C_{6-10}$ arylsulfinyl group, (xxi) a $C_{1-6}$ alkylsulfonyl group, (xxii) a $C_{6-10}$ arylsulfonyl group, (xxiii) amino, (xxiv) a $C_{1-6}$ acylamino group, (xxv) a mono- or di-$C_{1-6}$ alkylamino group, (xxvi) a $C_{3-8}$ cycloalkylamino group, (xxvii) a $C_{6-14}$ arylamino group, (xxviii) a $C_{1-6}$ alkyl-carbonyl group, (xxix) a $C_{1-6}$ alkyl-carbonyloxy group, (xxx) a $C_{6-10}$ aryl-carbonyl group, or (xxxi) a heterocyclic group, (3) a $C_{6-14}$ aryl group which may optionally be substituted with (i) a $C_{1-15}$ alkyl group which may optionally be substituted with halogen, (ii) a $C_{3-7}$ cycloalkyl group, (iii) a $C_{2-10}$ alkenyl group, (iv) a $C_{2-10}$ alkinyl group, (v) a $C_{3-10}$ cycloalkenyl group, (vi) a $C_{6-14}$ aryl group, (vii) a $C_{7-15}$ aralkyl group, (viii) nitro, (ix) hydroxy, (x) mercapto, (xi) oxo, (xii) thioxo, (xiii) cyano, (xiv) carbamoyl, (xv) carboxy, (xvi) a $C_{1-6}$ alkoxy-carbonyl group, (xvii) sulfo, (xviii) halogen, (xix) a $C_{1-6}$ alkoxy group, (xx) a $C_{6-20}$ aryloxy group, (xxi) a $C_{7-20}$ aralkyloxy group, (xxii) a $C_{1-6}$ acyloxy group, (xxiii) a $C_{1-6}$ alkylthio group, (xxiv) a $C_{6-10}$ arylthio group, (xxv) a $C_{1-6}$ alkylsulfinyl group, (xxvi) a $C_{6-10}$ arylsulfinyl group, (xxvii) a $C_{1-6}$ alkylsulfonyl group, (xxviii) a $C_{6-10}$ arylsulfonyl group, (xxix) amino, (xxx) a $C_{1-6}$ acylamino group, (xxxi) a mono- or di-$C_{1-6}$ alkylamino group, (xxxii) a $C_{3-8}$ cycloalkylamino group, (xxxiii) a $C_{6-14}$ arylamino group, (xxxiv) a $C_{1-6}$ alkyl-carbonyl group, (xxxv) a $C_{1-6}$ alkyl-carbonyloxy group, (xxxvi) a $C_{6-10}$ aryl-carbonyl group, or (xxxvii) a heterocyclic group, (4) a heterocyclic group, (5) a group of the formula —$NR^{24}R^{25}$, wherein $R^{24}$ and $R^{25}$ independently represent hydrogen or an optionally substituted $C_{6-14}$ aryl group, (6) a group of the formula —$OR^{26}$, wherein $R^{26}$ represents an optionally substituted $C_{1-15}$ alkyl group, a $C_{1-5}$ alkyl-carbonyl group, an optionally substituted $C_{6-14}$ aryl group, or an optionally substituted $C_{3-7}$ cycloalkyl group, or (7) a group of the formula —$SR^{27}$, wherein $R^{27}$ represents an optionally substituted $C_{6-14}$ aryl group, or an optionally substituted heterocyclic group, (8) the compound as described in (3), wherein $R^4$ represents (1) hydrogen, (2) a $C_{1-15}$ alkyl group which may optionally be substituted with (i) a $C_{3-7}$ cycloalkyl group, (ii) a $C_{3-10}$ cycloalkenyl group, (iii) nitro, (iv) hydroxy, (v) mercapto, (vi) oxo, (vii) thioxo, (viii) cyano, (ix) carbamoyl, (x) carboxy, (xi) a $C_{1-6}$ alkoxy-carbonyl group, (xii) sulfo, (xiii) halogen, (xiv) a $C_{1-6}$ alkoxy group, (xv) a $C_{6-20}$ aryloxy group, (xvi) a $C_{1-6}$ acyloxy group, (xvii) a $C_{1-6}$ alkylthio group, (xviii) a $C_{6-10}$ arylthio group, (xix) a $C_{1-6}$ alkylsulfinyl group, (xx) a $C_{6-10}$ arylsulfinyl group, (xxi) a $C_{1-6}$ alkylsulfonyl group, (xxii) a $C_{6-10}$ arylsulfonyl group, (xxiii) amino, (xxiv) a $C_{1-6}$ acylamino group, (xxv) a mono- or di-$C_{1-6}$ alkylamino group which may optionally be substituted with $C_{6-14}$ aryl, (xxvi) a $C_{3-8}$ cycloalkylamino group, (xxvii) a $C_{6-14}$ arylamino group, (xxviii) a $C_{1-6}$ alkyl-carbonyl group, (xxix) a $C_{1-6}$ alkyl-carbonyloxy group, (xxx) a $C_{6-10}$ aryl-carbonyl group, or (xxxi) a heterocyclic group which may optionally be substituted with $C_{7-15}$ aralkyl, (3) a $C_{7-15}$ aralkyl group which may optionally be substituted with (i) a $C_{1-15}$ alkyl group which may optionally be substituted with halogen, (ii) a $C_{3-7}$ cycloalkyl group, (iii) a $C_{2-10}$ alkenyl group, (iv) a $C_{2-10}$ alkinyl group, (v) a $C_{3-10}$ cycloalkenyl group, (vi) a $C_{6-14}$ aryl group, (vii) a $C_{7-15}$ aralkyl group, (viii) nitro, (ix) hydroxy, (x) mercapto, (xi) oxo, (xii) thioxo, (xiii) cyano, (xiv) carbamoyl, (xv) carboxy, (xvi) a $C_{1-6}$ alkoxy-carbonyl group, (xvii) sulfo, (xviii) halogen, (xix) a $C_{1-6}$ alkoxy group, (xx) a $C_{6-20}$ aryloxy group, (xxi) a $C_{7-20}$ aralkyloxy group, (xxii) a $C_{1-6}$ acyloxy group, (xxiii) a $C_{1-6}$ alkylthio group, (xxiv) a $C_{6-10}$ arylthio group, (xxv) a $C_{1-6}$ alkylsulfinyl group, (xxvi) a $C_{6-10}$ arylsulfinyl group, (xxvii) a $C_{1-6}$ alkylsulfonyl group, (xxviii) a $C_{6-10}$ arylsulfonyl group, (xxix) amino, (xxx) a $C_{1-6}$ acylamino group, (xxxi) a mono- or di-$C_{1-6}$ alkylamino group, (xxxii) a $C_{3-8}$ cycloalkylamino group, (xxxiii) a $C_{6-14}$ arylamino group, (xxxiv) a $C_{1-6}$ alkyl-carbonyl group, (xxxv) a $C_{1-6}$ alkyl-carbonyloxy group, (xxxvi) a $C_{6-10}$ aryl-carbonyl group, or (xxxvii) a heterocyclic group, (4) a $C_{1-15}$ alkyl-carbonyl group, (5) a $C_{1-15}$ alkoxy-carbonyl group, (6) a $C_{6-14}$ aryl-carbonyl group, (7) a $C_{6-14}$ aryl-oxycarbonyl group, (8) a $C_{7-15}$ aralkyl-carbonyl group, (9) a $C_{7-15}$ aralkyl-oxycarbonyl group, (10) carbamoyl which may optionally be substituted with $C_{1-15}$ alkylthio, or (11) a group of the formula —$SO_2$-$R^{23}$, wherein $R^{23}$ represents a $C_{6-14}$ aryl group which may optionally be substituted with $C_{1-6}$ alkyl; and $R^5$ and $R^6$ independently represent hydrogen, a $C_1 6$ alkyl group, a $C_{7-20}$ aralkyl group or a $C_{1-6}$ alkoxy-carbonyl group, (9) the compound as described in (1), wherein W is an oxygen atom,

(10) the compound as described in (1), wherein $R^1$ is (1) hydrogen, (2) a $C_{1-15}$ alkyl group which may optionally be substituted with $C_{1-6}$ alkoxy-carbonyl, or (3) a $C_{6-14}$ aryl group which may optionally be substituted with $C_{1-6}$ alkoxy; $R^2$ is (1) a $C_{6-14}$ aryl group which may optionally be substituted with the substituent selected from the group consisting of (i) hydroxy, (ii) halogen, (iii) a $C_{1-15}$ alkyl group, (iv) a $C_{3-7}$ cycloalkyl group, (v) a $C_{6-14}$ aryl group, (vi) a $C_{1-6}$ alkoxy group, (vii) a $C_{6-20}$ aryloxy group, (viii) a $C_{7-20}$ aralkyloxy group and (ix) a $C_{1-6}$ alkoxy group which may optionally be substituted with (a) a $C_{7-20}$ aralkyl-carbamoyl group, or (b) a heterocyclic group, (2) a $C_{1-15}$ alkyl group, (3) a $C_{1-15}$ alkoxy-carbonyl group, or (4) a heterocyclic group which may optionally be substituted with $C_{1-15}$ alkyl; $R^3$ is (1) hydrogen, (2) a $C_{1-15}$ alkyl group which may optionally be substituted with amino, (3) amino which may optionally be substituted with $C_{6-14}$ aryl, (4) a $C_{6-14}$ aryl group which may optionally be substituted with (i) hydroxy, (ii) halogen, (iii) a $C_{1-6}$ alkoxy group, or (iv) a $C_{1-6}$ alkyl-carbonyloxy group, (5) a group of the formula —O—$R^{28}$ wherein $R^{28}$ is (i) a $C_{1-15}$ alkyl group which may optionally be substituted with hydroxy, (ii) a $C_{6-14}$ aryl group which may optionally be substituted with halogen or hydroxy, (iii) a $C_{3-7}$ cycloalkyl group, or (iv) a $C_{1-6}$ alkyl-carbonyl group, (6) a group of the formula —S—$R^{29}$, wherein $R^{29}$ is a $C_{6-14}$ aryl group or a heterocyclic group, or (7) a heterocyclic group bonding through a carbon atom or a nitrogen atom, which may optionally be substituted with oxo,

(11) the compound as described in (3), wherein $R^4$ is (1) hydrogen, (2) a $C_{1-15}$ alkyl group which may optionally be substituted with (i) halogen, (ii) a $C_{1-6}$ alkoxy-carbonyl group, (iii) carbamoyl, (iv) a $C_{1-6}$ alkylamino group which may optionally be substituted with $C_{6-14}$ aryl, or (v) a heterocyclic group which may optionally be substituted with $C_{7-15}$ aralkyl, (3) a $C_{7-15}$ aralkyl group which may optionally be substituted with $C_{1-6}$ alkoxy, (4) a $C_{1-15}$ alkyl-carbonyl group, (5) a $C_{6-14}$ aryl-carbonyl group, (6) carbamoyl which may optionally be substituted with $C_{1-15}$ alkylthio, or (7) phenylsulfonyl which may optionally be substituted with $C_{1-6}$ alkyl; $R^5$ is hydrogen, a $C_{1-6}$ alkyl group, a $C_{7-20}$ aralkyl group or a $C_{1-6}$ alkoxy-carbonyl group; $R^6$ is hydrogen or a $C_{1-6}$ alkyl group,

(12) a compound of 8-(2-hydroxyphenyl)-5-phenyl-2-methyl-8H-[1,2,4]triazolo[3,4-c][1,4]thiazin-3(2H)-one or a salt thereof,

(13) a compound of 8-(2,3-dihydroxyphenyl)-5-phenyl-2-methyl-8H-[1,2,4]triazolo[3,4-c][1,4]thiazin-3(2H)-one or a salt thereof,

(14) a method of producing a compound of the formula:

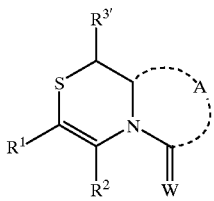

wherein $R^1$, $R^2$, W and A have the same meanings as defined in (1); and $R^{3'}$ is a group bonding through a carbon atom, a group bonding through a nitrogen atom, a group bonding through an oxygen atom or a group bonding through a sulfur atom; or a salt thereof, which comprises reacting a compound of the formula:

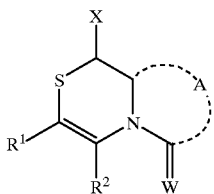

wherein X is a leaving group; $R^1{}_1$, $R^2$, W, and A have the same meanings as defined in (1); or a salt thereof with a compound of the formula:

wherein $R^3$ has the same meaning mentioned above; or a salt thereof,

(15) a method of producing the compound or a salt thereof as described in (4), which comprises subjecting a compound of the formula:

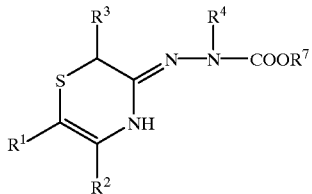

wherein $R^7$ is lower alkyl, preferably $C_{1-6}$ alkyl; $R^1$, $R^2$, and $R^3$ have the same meanings as defined in (4); $R^4$ has the same meaning as defined in (4); or a salt thereof to a cyclization reaction,

(16) a pharmaceutical composition comprising a compound or a salt thereof as claimed in claim 1 and a pharmaceutically acceptable carrier, excipient or diluent,

(17) a method for treating a mammal suffering from an abnormality in the balance of T helper-1 or T helper-2 cells derived from an immune disorder, which comprises administering an effective amount of a compound or salt thereof as claimed in claim 1 to said mammal,

(18) a method for inhibiting T helper-2 cell function in a mammal, which comprises administering to said mammal an effective amount of a compound or salt thereof as claimed in claim 1,

(19) a method for inhibiting splenocyte proliferative response, interleukin-5 production or interferon-gamma production in a mammal, which comprises administering to said mammal an effective amount of a compound or a salt thereof as claimed in claim 1,

(20) a method for treating or preventing allergic diseases or autoimmune diseases in a mammal, which comprises administering to said mammal an effective amount of a pharmaceutical composition as claimed in claim 22,

(21) a method for treating or preventing graft rejection or graft-vs-host disease in a mammal, which comprises administering to said mammal an effective amount of a pharmaceutical composition as claimed in claim 22.

DETAILED DESCRIPTION OF THE PREFERRED EMBODIMENT

The halogen atom of $R^3$ includes fluorine, chlorine, bromine, and iodine. Particularly preferred is chlorine.

The group bonding through a carbon atom for $R^1$, $R^2$, and $R^3$ can be any organic residue bonding through a carbon atom, thus including for example cyano, carboxy, an optionally substituted hydrocarbon group, an optionally substituted acyl group, an optionally substituted carbamoyl group, and a heterocyclic group bonding through a carbon atom.

The hydrocarbon group mentioned above includes an alkyl group, an alkenyl group, an alkinyl group, a cycloalkyl group, an aryl group, and an aralkyl group, and is preferably a $C_{1-24}$ hydrocarbon group especially preferably $C_{1-20}$ hydrocarbon group. The alkyl group that can be used includes a $C_{1-15}$ alkyl group, e.g. methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc., and is preferably a $C_{1-6}$ alkyl group such as methyl, ethyl, propyl, isopropyl, butyl, t-butyl, pentyl, hexyl, etc. The alkenyl group includes a $C_{2-10}$ alkenyl group, e.g. vinyl, allyl, 2-methylallyl, 2-butenyl, 3-butenyl, 3-octenyl, etc., and is preferably a $C_{2-6}$ alkenyl group, such as vinyl, butadienyl, hexatrienyl, etc. The alkinyl group includes a $C_{2-10}$ alkinyl group, e.g. ethinyl, 2-propinyl, isopropinyl, butinyl, t-butinyl, 3-hexinyl, etc., and is preferably a $C_{2-6}$ alkinyl group. The cycloalkyl group is preferably a $C_{3-7}$ cycloalkyl group, such as cyclopropyl, cyclopentyl, cyclohexyl, etc. The aryl group includes a $C_{6-14}$ aryl group such as phenyl, naphthyl, anthracenyl, etc. The aralkyl group includes a $C_{7-20}$ aralkyl group, such as benzyl, phenylethyl, phenylpropyl, 1-naphthylmethyl, 2-naphthylmethyl, benzhydryl, diphenylpropyl, diphenylbutyl, trityl, etc. Particularly preferred is a $C_{7-15}$ aralkyl group. Among the various hydrocarbon groups mentioned above, the alkyl group, the aryl group, and the aralkyl group are preferred.

The hydrocarbon group mentioned above may optionally has substitutions as described hereinafter.

The acyl group mentioned above includes a group of the formula —CO—$R^8$, wherein $R^8$ represents an optionally substituted hydrocarbon group or an optionally substituted hydrocarbon-oxy group. Preferred is a $C_{1-15}$ acyl group derived from $C_{1-15}$ aliphatic carboxylic acids.

The hydrocarbon group of the hydrocarbon group or hydrocarbon-oxy group for $R^8$ can be the same hydrocarbon group for the group bonding through a carbon atom mentioned above and may have substituents as described hereinafter.

The acyl group specifically includes a $C_{1-15}$ alkyl-carbonyl group such as formyl, acetyl, propionyl, butyryl, tert-butylcarbonyl, etc.; a $C_{1-15}$ alkoxy-carbonyl group such as acetoxy, ethoxycarbonyl, etc.; a $C_{6-14}$ aryl-carbonyl group such as benzoyl; a $C_{6-14}$ aryl-oxycarbonyl group such as benzoxycarbonyl; a $C_{7-15}$ aralkyl-carbonyl group such as benzylcarbonyl; and a $C_{7-15}$ aralkyl-oxycarbonyl group such as benzyloxycarbonyl.

The above-mentioned optionally substituted carbamoyl group includes a group of the formula—$CONR^9R^{10}$, wherein $R^9$ and $R^{10}$ independently represent an optionally substituted hydrocarbon group or an optionally substituted hydrocarbon-thio group.

Referring to the hydrocarbon group or hydrocarbon-thio group represented by $R^9$ or $R^{10}$, the hydrocarbon group may be the same hydrocarbon group as mentioned above for the group bonding through a carbon atom and may have substituent groups mentioned below.

Specifically, carbamoyl group which may optionally be substituted with, for example, $C_{1-15}$ alkyl, $C_{2-10}$ alkenyl, $C_{2-10}$ alkinyl, $C_{6-14}$ aryl, $C_{7-15}$ aralkyl, $C_{1-5}$ alkylthio, $C_{2-10}$ alkenylthio, $C_{2-10}$ alkinylthio, $C_{7-14}$ arylthio, or $C_{7-15}$ aralkylthio can be mentioned. Preferred species are a mono- or di-$C_{1-15}$ alkylcarbamoyl group, e.g. a mono- or di-$C_{1-6}$ alkylcarbamoyl group such as methylcarbamoyl, ethylcarbamoyl, hexylcarbamoyl, dimethylcarbamoyl, methylethylcarbamoyl, etc.; a mono- or di-$C_{1-15}$ alkylthiocarbamoyl group, e.g. a mono- or di-$C_{1-6}$ alkylthiocarbamoyl group such as methylthiocarbamoyl, ethylthiocarbamoyl, hexylthiocarbamoyl, dimethylthiocarbamoyl, methylthioethylthiocarbamoyl, etc.; and a mono- or di-$C_{7-15}$ aralkylcarbamoyl group, e.g. a $C_{7-13}$ aralkylcarbamoyl group such as benzylcarbamoyl, phenylethylcarbamoyl, phenylpropylcarbamoyl, benzhydrylcarbamoyl, etc.

The heterocyclic group bonding through a carbon atom includes a 3- to 8-membered heterocyclic group which contains 1 to 4 hetero atoms selected from a nitrogen atom, an oxygen atom, and a sulfur atom besides a carbon atom, or its condensed cyclic group.

Specifically, (1) a 5-membered cyclic group which contains 1 to 4 hetero atoms selected from oxygen atom, sulfur atom, and nitrogen atom besides carbon atom, such as 2- or 3-thienyl, 2- or 3-furyl, 2- or 3-pyrrolyl, 2-, 4-, or 5-oxazolyl, 2-, 4-, or 5-thiazolyl, 3-, 4-, or 5-pyrazolyl, 2-, 4-, or 5-imidazolyl, 3-, 4-, or 5-isoxazolyl, 3-, 4-, or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, etc.; (2) a 6-membered cyclic group which contains 1 to 4 hetero atoms selected from oxygen atom, sulfur atom, and nitrogen atom besides carbon atom, such as 2-, 3-, or 4-pyridyl, N-oxido-2-, 3- or 4-pyridyl, 2-, 4- or 5-pyrimidinyl, N-oxido-2-, 4- or 5-pyrimidinyl, 2- or 3-thiomorpholinyl, 2- or 3-morpholinyl, oxotriazinyl, dioxotriazinyl, 2- or 3-pyrrolidinyl, 2-, 3- or 4-piperidinyl, 2-, 3-, 4-, 5-or 6-pyranyl, thiopyranyl, 2- or 3-(1,4-oxazinyl), 2- or 3-(1,4-thiazinyl), 1,3-thiazinyl, 2- or 3-piperazinyl, triazinyl, oxotriazinyl, 3- or 4-pyridazinyl, 2- or 3-pyrazinyl, N-oxido-3- or 4-pyridazinyl, etc.; and (3) a 5- to 8-membered cyclic group which contains 1 to 4 hetero atoms selected from oxygen atom, sulfur atom, and nitrogen atom besides carbon atom or its condensed cyclic group, such as bicyclic or tricyclic condensed cyclic group which contains 1 to 4 hetero atoms selected from oxygen atom, sulfur atom, and nitrogen atom besides carbon atom, such as 2-, 3-, 4-, 5-, 6- or 7-benzofuranyl, 2-, 4-, 5-, 6- or 7-benzothiazolyl, 2-, 4-, 5-, 6- or 7-benzoxazolyl, tetrazolol,[1,5-b]pyridazinyl, triazolo[4,5-b]pyridazinyl, imidazo[1,2-a]pyridinyl, 2-, 4-, 5-, 6- or 7-benzimidazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 1-, 5- or 6-phthalazinyl, 2-, 4-, 5-, 6-, 7- or 8-quinazolinyl, 2-, 5- or 6-quinoxalinyl, 1-, 2-, 3-, 5-, 6-, 7- or 8-indolizinyl, 1-, 2-, 3-, 4-, 6-, 7-, 8- or 9-quinolizinyl, 2-, 3- or 4-(1,8-naphthyridinyl), 2-, 4-, 5-, 6- or 8-purinyl, 2-, 4-, 6- or 7-pteridinyl, 1-, 2-, 3- or 4-dibenzofuranyl, 1-, 2-, 3-, 4-, 5-, 6-, 7- or 8-carbazolyl, 1-, 2-, 3-, 4- or 9-acridinyl, 1-, 2-, 3-, 4-, 6- 7-, 8-, 9-, or 10-phenanthridinyl, 2-, 3-, 4-, 5-, 6-, 7- or 8-chromanyl, benzoxazidinyl, 1- or 2-phenazinyl, 1-, 2-, 3-, 4-, 6-, 7-, 8- or 9-phenothiazinyl, 1-, 2-, 3-, 4-, 6-, 7-, 8- or 9-phenoxazinyl, 1, 2- or 3, 4-methylenedioxyphenyl, etc. can be employed.

The above-mentioned (1) hydrocarbon group, (2) the hydrocarbon group mentioned for the hydrocarbon group or the hydrocarbon-oxy group of $R^8$ in the acyl group of the formula —CO—$R^8$, (3) the hydrocarbon group of the hydrocarbon group or hydrocarbon-thio group substituting said carbamoyl, or (4) the heterocyclic group bonding through a carbon atom may respectively have the following substituent groups (i)–(iv).

(i) The substituent for the cycloalkyl group, or aralkyl group, among said hydrocarbon group, is selected from the substituent group (hereinafter sometimes referred to briefly as substituent group A) consisting of a $C_{1-15}$ alkyl group, e.g. methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, pentadecyl, etc.; preferably a $C_{1-6}$ alkyl group, and which may optionally be substituted with halogen; a $C_{3-7}$ cycloalkyl group, e.g. cyclopropyl, cyclobutyl, cyclopentyl, cyclohexyl, etc.; a $C_{2-10}$ alkenyl group, e.g. vinyl, allyl, 2-methylallyl, 2-butenyl, 3-butenyl, 3-octenyl, etc.; a $C_{2-10}$ alkinyl group, e.g. ethinyl, 2-propinyl, 3-hexinyl, etc.; a $C_{3-10}$ cycloalkenyl group, e.g. cyclopropenyl, cyclopentenyl, cyclohexenyl, etc.; a $C_{6-14}$ aryl group, e.g. phenyl, naphthyl, etc.; a $C_{7-15}$ aralkyl group, e.g. benzyl, phenylethyl, trityl, etc.; nitro; hydroxy; mercapto; oxo; thioxo; cyano; carbamoyl; carboxy; a $C_{1-6}$ alkoxy-carbonyl group, e.g. methoxycarbonyl, ethoxycarbonyl, etc.; sulfo; halogen, e.g. fluorine, chlorine, bromine, iodine; a $C_{1-6}$ alkoxy group, e.g. methoxy, ethoxy, propoxy, isopropoxy, butoxy, isobutoxy, s-butoxy, t-butoxy, etc.; a $C_{6-20}$ aryloxy group, e.g. phenoxy biphenyloxy, naphthyloxy, etc.; a $C_{1-6}$ acyloxy group, e.g. acetoxy, propionyloxy, etc.; a $C_{1-6}$ alkylthio group, e.g. methylthio, ethylthio, n-propylthio, isopropylthio, n-butylthio, t-butylthio, etc.; a $C_{6-10}$ arylthio group, e.g. phenylthio etc.; a $C_{1-6}$ alkylsulfinyl group, e.g. methylsulfinyl, ethylsulfinyl, etc.; a $C_{6-10}$ arylsulfinyl group, e.g. phenylsulfinyl etc.; a $C_{1-6}$ alkylsulfonyl group, e.g. methylsulfonyl, ethylsulfonyl, etc.; a $C_{6-10}$ arylsulfonyl group, e.g. phenylsulfonyl etc.; amino; a $C_{1-6}$ acylamino group, e.g. acetylamino, propionylamino, etc.; a mono- or di-$C_{1-6}$ alkylamino group, e.g. methylamino, ethylamino, n-propylamino, isopropylamino, n-butylamino, dimethylamino, diethylamino, etc.; a $C_{3-8}$ cycloalkylamino group, e.g. cyclopropylamino, cyclobutylamino, cyclopentylamino, cyclohexylamino, etc.; a $C_{6-14}$ arylamino group, e.g. anilino etc.; a $C_{1-6}$ alkyl-carbonyl group, e.g. formyl, acetyl, hexanoyl, etc.; a $C_{1-6}$ alkyl-carbonyloxy group, e.g. acetyloxy, propionyloxy, etc.; a $C_{6-10}$ aryl-carbonyl group, e.g. benzoyl etc.; and a 5- or 6-membered heterocyclic group which contains 1 to 4 hetero atoms selected from oxygen atom, sulfur atom, and nitrogen atom besides carbon atom, e.g. 2- or 3-thienyl, 2- or 3-furyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 2-, 4-, or 5-imidazolyl, 1,2,3- or 1,2,4-triazolyl, 1H- or 2H-tetrazolyl, 2-, 3-, or 4-pyridyl, 2-, 4-, or 5-pyrimidinyl, 3- or 4-pyridazinyl, quinolyl, isoquinolyl, indolyl, etc.; the number of substituents may range from 1 to 6 and is preferably 1 to 3, and more preferably 1 or 2.

(ii) The substituent for the alkyl group, the alkenyl group, or the alkinyl group, among said hydrocarbon group, is selected from the substituent group (hereinafter sometimes referred to briefly as substituent group B) consisting of, for example above-mentioned $C_{3-7}$ cycloalkyl group, a $C_{3-10}$ cycloalkenyl group, nitro, hydroxy, mercapto, oxo, thioxo, cyano, carbamoyl, carboxy, a $C_{1-6}$ alkoxy-carbonyl group, sulfo, halogen, a $C_{1-6}$ alkoxy group, a $C_{6-20}$ aryloxy group, a $C_{1-6}$ acyloxy group, a $C_{1-6}$ alkylthio group, a $C_{6-10}$ arylthio group, a $C_{1-6}$ alkylsulfinyl group, a $C_{6-10}$ arylsulfinyl group, a $C_{1-6}$ alkylsulfonyl group, a $C_{6-10}$ arylsulfonyl group, amino, a $C_{1-6}$ acylamino group, a mono- or di-$C_{1-6}$ alkylamino group, a $C_{3-8}$ cycloalkylamino group, a $C_{6-14}$ arylamino group, a $C_{1-6}$ alkyl-carbonyl group, a $C_{1-6}$ alkyl-carbonyloxy group, a $C_{6-10}$ aryl-carbonyl group, and a 5- or 6-membered heterocyclic group which contains 1 to 4 hetero atoms selected from oxygen atom, sulfur atom, and nitrogen atom besides carbon atom. The number of substituents is 1 to 6, preferably 1 to 3, and more preferably 1 or 2.

(iii) The substituent for the aryl group, among said hydrocarbon group, is selected from the substituent group (hereinafter sometimes referred to briefly as substituent group C) consisting of, for example above-mentioned, (1) a $C_{1-15}$ alkyl group which may optionally be substituted with halogen, (2) a $C_{3-7}$ cycloalkyl group, (3) a $C_{2-10}$ alkenyl group, (4) a $C_{2-10}$ alkinyl group, (5) a $C_{3-10}$ cycloalkenyl group, (6) a $C_{6-14}$ aryl group, (7) a $C_{7-15}$ aralkyl group, (8) nitro, (9) hydroxy, (10) mercapto, (11) oxo, (12) thioxo, (13) cyano, (14) carbamoyl, (15) carboxy, (16) a $C_{1-6}$ alkoxy-carbonyl group, (17) sulfo, (18) halogen, (19) a $C_{1-6}$ alkoxy group which may optionally be substituted with (a) a group of the formula —CONR$^{21}$R$^{22}$, wherein R$^{21}$ and R$^{22}$ independently represent a hydrogen atom, a $C_{1-6}$ alkyl group, a $C_{1-6}$ alkoxy group, a $C_{3-7}$ cycloalkyl group, a $C_{6-14}$ aryl group or a $C_{7-20}$ aralkyl group, or (b) a 3- to 8-membered heterocyclic group which contains 1 to 4 hetero atoms selected from oxygen atom, sulfur atom, and nitrogen atom besides carbon atom or its condensed cyclic group, (20) a $C_{6-20}$ aryloxy group which may optionally be substituted with substituents selected from substituent group A as described above, (21) a $C_{7-20}$ aralkyloxy group which may optionally be substituted with substituents selected from substituent group A as described above, e.g. benzyloxy, phenylethyloxy, benzhydryloxy, trityloxy, 1-naphthyloxy, 2-naphthyloxy, etc; (22) a $C_{1-6}$ acyloxy group, (23) a $C_{1-6}$ alkylthio group, (24) a $C_{6-10}$ arylthio group, (25) a $C_{1-6}$ alkyl sulfinyl group, (26) a $C_{6-10}$ arylsulfinyl group, (27) a $C_{1-6}$ alkylsulfonyl group, (28) a $C_{6-10}$ arylsulfonyl group, (29) amino, (30) a $C_{1-6}$ acylamino group, (31) a mono- or di-$C_{1-6}$ alkylamino group, (32) a $C_{3-8}$ cycloalkylamino group, (33) a $C_{6-14}$ arylamino group, (34) a $C_{1-6}$ alkyl-carbonyl group, (35) a $C_{1-6}$ alkyl-carbonyloxy group, (36) a $C_{6-10}$ aryl-carbonyl group, and (37) a 5- or 6-membered heterocyclic group which contains 1 to 4 hetero atoms selected from oxygen atom, sulfur atom, and nitrogen atom besides carbon atom. The number of substituents is 1 to 6, preferably 1 to 3, and more preferably 1 or 2.

(iv) The heterocyclic group bonding through a carbon atom may have substituent similar to the substituent selected from the substituent group A as mentioned in (i) above.

The number of substituents is 1 to 6, preferably 1 to 3, and more preferably 1 or 2.

The group bonding through a nitrogen atom for R$^1$, R$^2$, or R$^3$ includes all groups bonding through a nitrogen atom.

Specifically, (1) nitro, (2) a group of the formula —NR$^{11}$R$^{12}$, wherein R$^{11}$ and R$^{12}$ independently represent hydrogen atom, an optionally substituted hydrocarbon group, an optionally substituted acyl group, an optionally substituted heterocyclic group, hydroxy, or an optionally substituted hydrocarbon-oxy group, (3) an optionally substituted heterocyclic group bonding through a nitrogen atom, or (4) a group of the formula —N=C (R$^{13}$)R$^{14}$, wherein R$^{13}$ and R$^{14}$ independently represent hydrogen atom, an optionally substituted hydrocarbon group, an optionally substituted heterocyclic group, an optionally substituted acyl group, hydroxy, an optionally substituted hydrocarbon-oxy group, or a group of the formula —NR$^{15}$R$^{16}$, wherein R$^{15}$ and R$^{16}$ independently represent hydrogen atom, an optionally substituted hydrocarbon group, an optionally substituted heterocyclic group, or an optionally substituted acyl group, can be used.

The optionally substituted hydrocarbon group for R$^{11}$, R$^{12}$, R$^{13}$, R$^{14}$, R$^{15}$, or R$^{16}$ includes the same optionally substituted hydrocarbon groups as mentioned for the group bonding through a carbon atom.

Referring to the optionally substituted hydrocarbon-oxy group mentioned for R$^{11}$, R$^{12}$, R$^{13}$, or R$^{14}$, the hydrocarbon group which may optionally be substituted includes the same optionally substituted hydrocarbon group as mentioned for the group bonding through a carbon atom.

The optionally substituted acyl group for R$^{11}$, R$^{12}$, R$^{13}$, R$^{14}$, R$^{15}$, or R$^{16}$ includes the same optionally substituted acyl group as mentioned for the group bonding through a carbon atom.

The heterocyclic group bonding through a nitrogen atom as mentioned above for the group bonding through a nitrogen atom is a 3- to 8-membered cyclic group which contains 1 to 4 hetero atoms selected from nitrogen atom, oxygen atom, and sulfur atom besides carbon atom and one nitrogen atom, or its condensed cyclic group, and specifically includes 1H-1-pyrrolyl, 1-imidazolyl, 1-triazolyl, 1-pyrazolyl, 1-indolyl, 1H-1-indazolyl, 7-purinyl, 1-aziridinyl, 1-pyrrolidinyl, 1-pyrrolinyl, 1-imidazolidinyl, 2-isoxazolyl, 1-pyrazolidinyl, 1-piperazinyl, 1- or 2-pyrazolinyl, 1-piperidyl, 4-morpholinyl, 4-thiomorpholinyl, 1-quinolyl, 1-imidazolinyl, 1-indolinyl, 1-pyridyl, 1-pyrimidinyl, 1-pyridazinyl, 2-isothiazolyl, 1-pyrazinyl and 2-furazanyl.

The heterocyclic group for R$^{11}$, R$^{12}$, R$^{13}$, R$^{14}$, R$^{15}$, or R$^{16}$ includes 3- to 8-membered cyclic group which contains 1 to 4 hetero atoms selected from nitrogen atom, oxygen atom, and sulfur atom besides carbon atom or its condensed cyclic group. Among them are 5- to 8-membered cyclic group which contains 1 to 4 hetero atoms selected from oxygen atom, sulfur atom, and nitrogen atom besides carbon atom or its condensed cyclic group, such as 5-membered cyclic group which contains 1 to 4 hetero atoms selected from oxygen atom, sulfur atom, and nitrogen atom besides carbon atom, such as thienyl, furyl, pyrrolyl, pyrrolidinyl, oxazolyl, thiazolyl, pyrazolyl, imidazolyl, isoxazolyl, isothiazolyl, 1,2,4-oxadiazolyl, 1,3,4-oxadiazolyl, 1,2,4-thiadiazolyl, 1,3,4-thiadiazolyl, 1,2,3-thiadiazolyl, 1,2,5-thiadiazolyl, 1,2,3-triazolyl, 1,2,4-triazolyl, 1H- or 2H-tetrazolyl, furazanyl, pyrrolinyl, imidazolidinyl, imidazolinyl, pyrazolidinyl, pyrazolinyl, etc.; 6-membered cyclic group which contains 1 to 4 hetero atoms selected from oxygen atom, sulfur atom, and nitrogen atom besides carbon atom, such as pyridyl, N-oxido-2-, 3-, or 4-pyridyl, pyrimidinyl, N-oxido-2-, 4-, or 5-pyrimidinyl, thiomorpholinyl, morpholinyl, oxotriazinyl, dioxo-triazinyl, piperidyl, pyranyl, thiopyranyl, 1,4-oxazinyl, 1,4-thiazinyl, 1,3-thiazinyl, piperazinyl, triazinyl, oxotriazinyl, pyridazinyl, pyrazinyl, N-oxido-3- or 4-pyridazinyl, etc.; and bicyclic or tricyclic condensed cyclic group which contains 1 to 4 hetero atoms selected from oxygen atom, sulfur atom, and nitrogen atom besides carbon atom, such as benzofuryl, benzothiazolyl, benzoxazolyl, tetrazolo[1,5-b]pyridazinyl, triazolo[4,5-b] pyridazinyl, imidazo[1,2-a]pyridinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, chromanyl, benzoxazinyl, phenazinyl, phenothiazinyl, and phenoxazinyl, among others.

The substituent group that may be present on said heterocyclic group or said heterocyclic group bonding through a nitrogen atom includes a $C_{1-6}$ alkyl group which may optionally be substituted with halogen, e.g. methyl, ethyl, propyl, isopropyl, butyl, isobutyl, sec-butyl, tert-butyl, etc.; a $C_{2-6}$ alkenyl group, e.g. vinyl, 1-methylvinyl, 1-propenyl, allyl, etc.; a $C_{2-6}$ alkinyl group, e.g. ethinyl, 1-propinyl, propargyl, etc.; a $C_{3-6}$ cycloalkyl group, e.g. cyclopropyl, cyclobutyl, cyclopentyl, cyclohexyl, etc.; a $C_{5-7}$ cycloalkenyl group, e.g. cyclopentenyl, cyclohexenyl, etc.; a $C_{7-11}$ aralkyl group, e.g. benzyl, α-methylbenzyl, phenethyl, etc.; a $C_{6-14}$ aryl group, e.g. phenyl, naphthyl, etc.; a $C_{1-6}$ alkoxy group, e.g. methoxy, ethoxy, propoxy, iso-propoxy, n-butoxy, iso-butoxy, sec-butoxy, tert-butoxy, etc.; a $C_{6-20}$ aryloxy group, e.g. phenoxy etc.; a $C_{1-6}$ alkyl-carbonyl group, e.g. formyl, acetyl, propionyl, n-butyryl, iso-butyryl, etc.; a $C_{6-14}$ aryl-carbonyl gorup, e.g. benzoyl etc.; a $C_{1-6}$ alkyl-carbonyloxy group, e.g. formyloxy, acetyloxy, propionyloxy, n-butyryloxy, isobutyryloxy, etc.; a $C_{6-14}$ aryl-carbonyloxy group, e.g. benzoyloxy etc.; carboxy; a $C_{1-6}$ alkoxy-carbonyl group, e.g. methoxycarbonyl, ethoxycarbonyl, n-propoxycarbonyl, isopropoxycarbonyl, n-butoxycarbonyl, isobutoxycarbonyl, tert-butoxycarbonyl, etc.; carbamoyl; a N-mono-$C_{1-4}$ alkyl-carbamoyl group, e.g. N-methylcarbamoyl, N-ethylcarbamoyl, N-propylcarbamoyl, N-isopropylcarbamoyl, N-butylcarbamoyl, etc.; a N,N-di-$C_{1-4}$ alkylcarbamoyl group, e.g. N,N-dimethylcarbamoyl, N,N-diethylcarbamoyl, N,N-dipropylcarbamoyl, N,N-dibutylcarbamoyl, N,N-dipropylcarbamoyl, N,N-dibutylcarbamoyl, etc.; a cycloaminocarbonyl group, e.g. 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, etc.; halogen, e.g. fluorine, chlorine, bromine, iodine; a mono-, di-, or tri-halo-$C_{1-4}$ alkyl group, e.g. chloromethyl, dichloromethyl, trifluoromethyl, trifluoroethyl, etc.; oxo; amidino; imino; alkylimino, e.g. methylimino, ethylimino, propylimino, butylimino, etc.; amino; a mono- or di-$C_{1-6}$ alkylamino group, e.g. methylamino, ethylamino, propylamino, isopropylamino, butylamino, dimethylamino, diethylamino, dipropylamino, diisopropylamino, dibutylamino, etc.; 3- to 6-membered cyclic amino group which contains 1 to 3 hetero atoms selected from oxygen atom, sulfur atom, and nitrogen atom besides carbon atom and one nitrogen atom, e.g. aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl, etc.; a $C_{1-6}$ alkyl-carbonylamino group, e.g. formamido, acetamido, trifluoroacetamido, propionylamido, butyrylamido, isobutyrylamido, etc.; benzamido; carbamoylamino; a N-$C_{1-4}$ alkylcarbamoylamino group, e.g. N-methylcarbamoylamino, N-ethylcarbamoylamino, N-propylcarbamoylamino, N-isopropylcarbamoylamino, N-butylcarbamoylamino, etc.; a N,N-di-$C_{1-4}$ alkylcarbamoyl-amino group, e.g. N,N-dimethylcarbamoylamino, N,N-diethylcarbamoylamino, N,N-dipropylcarbamoylamino, N,N-dibutylcarbamoylamino, etc.; a $C_{1-3}$ alkylenedioxy group, e.g. methylenedioxy, ethylenedioxy, etc.; —$B(OH)_2$; hydroxy; epoxy(—O—); nitro; cyano; mercapto; sulfo; sulfino; phosphono; dihydroxyboryl; sulfamoyl; a $C_{1-6}$ alkylsulfamoyl group, e.g. N-methylsulfamoyl, N-ethylsulfamoyl, N-propylsulfamoyl, N-isopropylsulfamoyl, N-butylsulfamoyl, etc.; a di-$C_{1-6}$ alkylsulfamoyl group, e.g. N,N-dimethylsulfamoyl, N,N-diethylsulfamoyl, N,N-dipropylsulfamoyl, N,N-dibutylsulfamoyl, etc.; a $C_{1-6}$ alkylthio group, e.g. methylthio, ethylthio, propylthio, isopropylthio, n-butylthio, sec-butylthio, tert-butylthio, etc.; a $C_{6-11}$ arylthio group, e.g. phenylthio etc.; a $C_{1-6}$ alkylsulfinyl group, e.g. methylsulfinyl, ethylsulfinyl, propylsulfinyl, butylsulfinyl, etc.; a $C_{6-14}$ arylsulfinyl group, e.g. phenylsulfinyl etc.; a $C_{1-6}$ alkylsulfonyl group, e.g. methylsulfonyl, ethylsulfonyl, propylsulfonyl, butylsulfonyl, etc.; a $C_{6-14}$ arylsulfonyl group, e.g. phenylsulfonyl etc. can be mentioned. The number of substituents may range from 1 to 6 within the substitutable range and is preferably 1 to 3.

The group bonding through an oxygen atom for $R^1$, $R^2$, or $R^3$ includes all groups bonding through an oxygen atom. Thus, for example, a group of the formula —$OR^{17}$, wherein $R^{17}$ represents (1) hydrogen, (2) an optionally substituted hydrocarbon group, (3) an optionally substituted heterocyclic group, (4) an optionally substituted acyl group, or (5) a group of the formula—$NR^{18}R^{19}$, wherein $R^{18}$ and $R^{19}$ independently represent hydrogen, an optionally substituted hydrocarbon group, an optionally substituted heterocyclic group, or an optionally substituted acyl group can be employed.

The optionally substituted hydrocarbon group for $R^{17}$, $R^{18}$, or $R^{19}$ can be the same optionally substituted hydrocarbon groups as mentioned hereinbefore for the group bonding through a carbon atom.

The optionally substituted heterocyclic group for $R^{17}$, $R^{18}$, or $R^{19}$ above includes the same optionally substituted heterocyclic groups as mentioned for $R^{11}$, $R^{12}$, $R^{13}$, $R^{14}$, $R^{15}$, or $R^{16}$.

The optionally substituted acyl group for $R^{17}$, $R^{18}$, or $R^{19}$ includes the same optionally substituted acyl groups mentioned above for the group bonding through a carbon atom.

The group bonding through a sulfur atom for $R^1$, $R^2$, or $R^3$ includes all groups bonding through a sulfur atom. For example, a group of the formula —$S(O)_nR^{20}$, wherein $R^{20}$ represents an optionally substituted hydrocarbon group or an optionally substituted heterocyclic group; n represents an integer of 0 to 2.

The optionally substituted hydrocarbon group for $R^{20}$ includes the same optionally substituted hydrocarbon groups as mentioned for the group bonding through a carbon atom.

The optionally substituted heterocyclic group for $R^{20}$ includes the same optionally substituted heterocyclic groups as mentioned for $R^{11}$, $R^{12}$, $R^{13}$, $R^{14}$, $R^{15}$, $R^{16}$.

Preferred examples of the group bonding through a sulfur atom are alkylthio which may optionally be substituted, cycloalkylthio which may optionally be substituted, arylthio which may optionally be substituted, aralkylthio which may optionally be substituted, heterocycle-thio which may optionally be substituted, alkylsulfinyl which may optionally be substituted, alkylsulfonyl which may optionally be substituted, and arylsulfonyl which may optionally be substituted.

The group forming a nitrogen-containing condensed ring at the 3,4-position of a 1,4-thiazine ring for A is the condensed cyclic group which contains only nitrogen atom as hetero atom, and preferably the partial structure

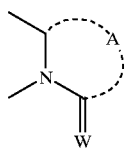

represents a 5- or 6-membered ring containing 1 to 3 nitrogen atoms and substituted with oxo or thioxo.

Specifically, the group of the formula

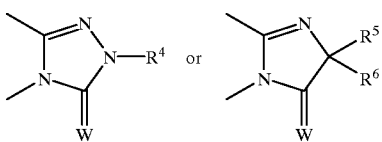

wherein $R^4$ represents hydrogen, a group bonding through a carbon atom or a group bonding through a sulfur atom; $R^5$ and $R^6$ independently represent hydrogen, a group bonding through a carbon atom, a group bonding through a nitrogen atom, a group bonding through an oxygen atom, or a group bonding through a sulfur atom; W represents an oxygen atom or a sulfur atom can be mentioned.

The group bonding through a carbon atom and the group bonding through a sulfur atom, both mentioned for $R^4$, $R^5$, or $R^6$ above, include the same groups bonding through a carbon atom and groups bonding through a sulfur atom as mentioned for $R^1$, $R^2$ or $R^3$ hereinbefore.

The group bonding through a nitrogen atom and the group bonding through an oxygen atom, both mentioned for $R^5$ or $R^6$ above, include the same groups bonding through a nitrogen atom and groups bonding through an oxygen atom as mentioned for $R^1$, $R^2$ or $R^3$ hereinbefore.

Referring to the bivalent hydrocarbon group interrupted by one or more hetero atoms as formed by combining $R^1$ and $R^2$, the hetero atom may be 1 to 3, and may be selected from a nitrogen atom, an oxygen atom, and a sulfur atom. The bivalent hydrocarbon group may for example be a $C_{2-6}$ saturated or unsaturated hydrocarbon group and is preferably a $C_{2-6}$ alkylene group, a $C_{2-6}$ alkenylene group, or a $C_{2-6}$ alkinylene group.

Specifically, the partial structural formula:

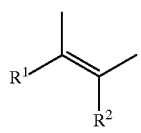

may for example represent a group of the formula:

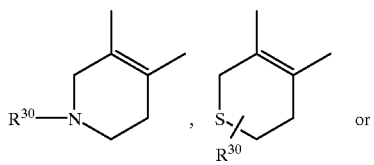

-continued

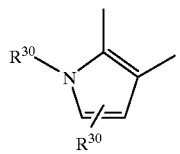

wherein $R^{30}$ represents a substituent.

The alkylene group formed by combining $R^1$ and $R^2$ is preferably a $C_{2-6}$ alkylene group and, especially preferably a $C_{3-5}$ alkylene group.

Specifically, the partial structural formula:

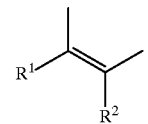

may for example represent a group of the formula:

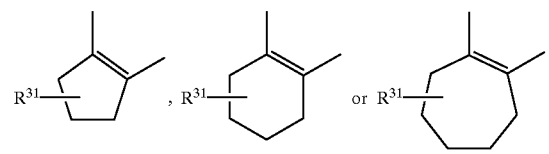

wherein $R^{31}$ represents a substituent.

The substituent of $R^{30}$ or $R^{31}$ for the bivalent hydrocarbon group interrupted by one or more hetero atoms or the alkylene group includes the same substituents which includes above-mentioned substitutent group A as mentioned for the cycloalkyl, and aralkyl groups among the hydrocarbon groups bonding through a carbon atom.

Among the above-mentioned various groups, $R^1$ is preferably hydrogen, an optionally substituted hydrocarbon group, an optionally substituted acyl group, an optionally substituted carbamoyl group, a group of the formula $-NR^{11}R^{12}$, wherein $R^{11}$ and $R^{12}$ are as defined hereinbefore, or an optionally substituted heterocyclic group bonding through a carbon atom. More specifically, $R^1$ is preferably (1) hydrogen, (2) a $C_{1-15}$ alkyl group which may optionally be substituted with substituents selected from above-mentioned substituent group B, (3) a $C_{6-14}$ aryl group which may optionally be substituted with substituents selected from above-mentioned substituent group A, (4) a $C_{1-15}$ acyl group, (5) a carbamoyl group, (6) a group of the formula $-NR^{100}R^{101}$ wherein $R^{100}$ and $R^{101}$ independently represent hydrogen, an optionally substituted $C_{1-15}$ alkyl group, or an optionally substituted $C_{6-14}$ aryl group, (7) a 3- to 8-membered heterocyclic group which contains 1 to 4 hetero atoms selected from nitrogen atom, oxygen atom, and sulfur atom besides carbon atom or its condensed cyclic group.

Particularly preferred are (1) hydrogen, (2) a $C_{1-15}$ alkyl group which may optionally be substituted with substituents selected from above-mentioned substituent group B, and (3) a $C_{6-14}$ aryl group which may optionally be substituted with substituents selected from above-mentioned substituent group A.

Especially preferred is (1) hydrogen, (2) a $C_{1-15}$ alkyl group which may optionally be substituted with $C_{1-6}$ alkoxy-carbonyl, (3) a $C_{6-14}$ aryl group which may optionally be substituted with $C_{1-6}$ alkoxy.

Among the various groups mentioned hereinbefore, $R^2$ is preferably hydrogen, an optionally substituted hydrocarbon group, an optionally substituted acyl group, or an optionally substituted heterocyclic group bonding through a carbon atom. More specifically, $R^2$ is preferably (1) hydrogen, (2) an optionally substituted $C_{1-15}$ alkyl gorup, (3) an optionally substituted $C_{6-14}$ aryl group, (4) an optionally substituted $C_{1-15}$ acyl group, (5) an optionally substituted 3- to 8-membered heterocyclic group which contains 1 to 4 hetero atoms selected from nitrogen atom, oxygen aotm, and sulfur atom besides carbon atom or its condensed cyclic group.

More specifically $R^2$ is (1) hydrogen, (2) a $C_{1-15}$ alkyl group which may optionally be substituted with substituents selected from above-mentioned substituent group B, (3) a $C_{6-14}$ aryl group which may optionally be substituted with substituents selected from above-mentioned substituent group C, (4) a group of the formula —$COOR^{102}$, wherein $R^{102}$ represents hydrogen or a $C_{1-15}$ alkyl group, or (5) a 3- to 8-membered heterocyclic group which contains 1 to 4 hetero atoms selected from nitrogen atom, oxygen atom, and sulfur atom besides carbon atom, or its condensed cyclic group, which may optionally be substituted with $C_{1-15}$ alkyl, preferably with $C_{1-6}$ alkyl.

Especially preferred is (1) a $C_{6-14}$ aryl group which may optionally be substituted with the substituent selected from the group consisting of (i) hydroxy, (ii) halogen, (iii) a $C_{1-15}$ alkyl group, (iv) a $C_{3-7}$ cycloalkyl group, (v) a $C_{6-14}$ aryl group, (vi) a $C_{1-6}$ alkoxy group, (vii) a $C_{6-20}$ aryloxy group, (viii) a $C_{7-20}$ aralkyloxy group and (ix) a $C_{1-6}$ alkoxy group which may optionally be substituted with (a) a $C_{7-20}$ aralkyl-carbamoyl group, or (b) a 5- or 6-membered heterocyclic group which contains 1 to 4 hetero atoms selected from nitrogen atom, oxygen atom, and sulfur atom besides carbon atom, or its condensed cyclic group, (2) a $C_{1-15}$ alkyl group, (3) a $C_{1-15}$ alkoxy-carbonyl group, or (4) a 3- to 8-membered heterocyclic group which contains 1 to 4 hetero atoms selected from oxygen atom, sulfur atom, and nitrogen atom besides carbon atom or its condensed cyclic group, which may optionally be substituted with $C_{1-15}$ alkyl.

Among the various groups mentioned hereinbefore, the preferred group for $R^3$ is hydrogen, an optionally substituted hydrocarbon group, a group of the formula—$NR^{11}R^{12}$, wherein $R^{11}$ and $R^{12}$ are as defined hereinbefore, an optionally substituted heterocyclic group bonding through a carbon atom, a group of the formula —$OR^{17}$, wherein $R^{17}$ is as defined hereinbefore, or a group of the formula —$S(O)_n R^{20}$, wherein $R^{20}$ and n are as defined hereinbefore. More specifically, $R^3$ is preferably (1) hydrogen, (2) an optionally substituted $C_{1-15}$ alkyl group, (3) a group of the formula —$NR^{103}R^{104}$, wherein $R^{103}$ and $R^{104}$ independently represent hydrogen, a $C_{1-15}$ alkyl group, an optionally substituted $C_{6-14}$ aryl group, or a group of the formula —$(CH_2)_q$-$R^{105}$, wherein q represents an integer of 1 to 6; $R^{105}$ represents a $C_{6-14}$ aryl group or a 3- to 8-membered heterocyclic group which contains 1 to 4 hetero atoms selected from nitrogen atom, oxygen atom, and sulfur atom besides carbon atom or its condensed cyclic group, (4) an optionally substituted $C_{6-14}$ aryl group, (5) a 3- to 8-membered heterocyclic group which contains 1 to 4 hetero atoms selected from nitrogen atom, oxygen atom, and sulfur atom besides carbon atom or its condensed cyclic group, (6) a group of the formula —$OR^{106}$, wherein $R^{106}$ represents hydrogen, an optionally substituted $C_{1-15}$ alkyl group, an optionally substituted $C_{6-14}$ aryl group, an optionally substituted $C_{1-15}$ alkyl-carbonyl group, an optionally substituted $C_{3-7}$ cycloalkyl group, or a group of the formula —$(CH_2)_r$-$R^{107}$, wherein r represents an integer of 1 to 6; $R^{107}$ represents halogen, hydroxy, a $C_{6-14}$ aryl group or a 3- to 8-membered heterocyclic group or its condensed cyclic group, or (7) a group of the formula—$SR^{108}$, wherein $R^{108}$ represents hydrogen, a $C_{1-15}$ alkyl group, an optionally substituted $C_{6-14}$ aryl group, an optionally substituted 3- to 8-membered heterocyclic group which contains 1 to 4 hetero atoms selected from nitrogen atom, oxygen atom, and sulfur atom besides carbon atom or its condensed cyclic group, or a group of the formula —$(CH_2)_s$-$R^{109}$, wherein s represents an integer of 1 to 6; $R^{109}$ represents a $C_{6-14}$ aryl group or a 3- to 8-membered heterocyclic group which contains 1 to 4 hetero atoms selected from nitrogen atom, oxygen atom, and sulfur atom besides carbon atom, or its condensed cyclic group.

More specifically, the preferred group for $R^3$ is (1) hydrogen, (2) a $C_{1-15}$ alkyl group which may optionally be substituted with substituents selected from above-mentioned substituent group B, (3) a $C_{6-14}$ aryl group which may optionally be substituted with substituents selected from above-mentioned substituent group A, (4) a 3- to 8-membered heterocyclic group which contains 1 to 4 hetero atoms selected from nitrogen atom, oxygen atom, and sulfur atom besides carbon atom, or its condensed cyclic group, (5) a group of the formula —$NR^{24}R^{25}$, wherein $R^{24}$ and $R^{25}$ independently represent hydrogen or a $C_{6-14}$ aryl group which may optionally be substituted with substituents selected from above-mentioned substituent group A, (6) a group of the formula —$OR^{26}$, wherein $R^{26}$ represents a $C_{1-15}$ alkyl group which may optionally be substituted with substituents selected from above-mentioned substituent group B, a $C_{1-15}$ alkyl-carbonyl group, a $C_{6-14}$ aryl group which may optionally be substituted with substituents selected from above-mentioned substituent group A, or a $C_{3-7}$ cycloalkyl group which may optionally be substituted with substituents selected from above-mentioned substituent group A, or (7) a group of the formula —$SR^{27}$, wherein $R^{27}$ represents a $C_{6-14}$ aryl group which may optionally be substituted with substituents selected from above-mentioned substituent group A or a heterocyclic group which may optionally be substituted with substituents selected from above-mentioned substituent group B.

Particularly preferred is (1) hydrogen, (2) a $C_{1-15}$ alkyl group which may optionally be substituted with amino, (3) amino which may optionally be substituted with $C_{6-14}$ aryl group, (4) a $C_{6-14}$ aryl group which may optionally be substituted with (i) hydroxy, (ii) halogen, (iii) a $C_{1-6}$ alkoxy group, or (iv) a $C_{1-6}$ alkyl-carbonyloxy group, (5) a group of the formula —O—$R^{28}$, wherein $R^{28}$ represents (i) a $C_{1-15}$ alkyl group which may optionally be substituted with hydroxy, (ii) a $C_{6-4}$ aryl group which may optionally be substituted with halogen or hydroxy, (iii) a $C_{3-7}$ cycloalkyl group, or (iv) a $C_{1-6}$ alkyl-carbonyl group, (6) a group of the formula —S—$R^{29}$, wherein $R^{29}$ represents a $C_{6-14}$ aryl group or a heterocyclic group, or (7) a 3- to 8-membered heterocyclic group bonding through a carbon atom or a nitrogen atom, which contains 1 to 4 hetero atoms selected from nitrogen atom, oxygen atom, and sulfur atom besides carbon atom or its condensed cyclic group, which may optionally be substituted with oxo.

When $R^3$ represents an elimination group such as halogen or a $C_{1-14}$ acyloxy group, e.g. a $C_{1-6}$ alkyl-carbonyloxy group, a $C_{6-14}$ aryl-carbonyloxy group, etc., the compound is also useful as a novel intermediate for the production of compound [I] wherein $R^3$ is a different functional group.

As the group forming a nitrogen-containing condensed ring at the 3,4-position of the 1,4-thiazine ring for A, the partial structure of the formula:

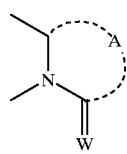

is preferably a group of the formula:

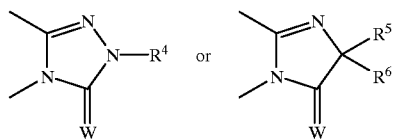

wherein $R^4$, $R^5$, $R^6$, and W are as defined hereinbefore. Particularly preferred is a group of the formula:

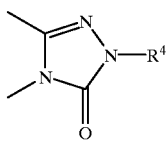

wherein $R^4$ is as defined hereinbefore.

$R^4$ is preferably hydrogen, an optionally substituted hydrocarbon group, an optionally substituted acyl group, or an optionally substituted carbamoyl group. More specifically, $R^4$ is preferably (1) hydrogen, (2) an optionally substituted $C_{1-15}$ alkyl group, (3) an optionally substituted $C_{7-15}$ aralkyl group, (4) an optionally substituted $C_{1-15}$ acyl group, (5) an optionally substituted carbamoyl group, or (6) a group of the formula —$SO_2$-$R^{23}$, wherein $R^{23}$ is a $C_{6-14}$ aryl group which may optionally be substituted with $C_{1-6}$ alkyl. Particularly preferred is (1) hydrogen, (2) a $C_{1-15}$ alkyl group which may optionally be substituted with (i) a $C_{3-7}$ cycloalkyl group, (ii) a $C_{3-10}$ cycloalkenyl group, (iii) nitro, (iv) hydroxy, (v) mercapto, (vi) oxo, (vii) thioxo, (viii) cyano, (ix) carbamoyl, (x) carboxy, (xi) a $C_{1-6}$ alkoxy-carbonyl group, (xii) sulfo, (xiii) halogen, (xiv) a $C_{1-6}$ alkoxy group, (xv) a $C_{6-20}$ aryloxy group, (xvi) a $C_{1-6}$ acyloxy group, (xvii) a $C_{1-6}$ alkylthio group, (xviii) a $C_{6-10}$ arylthio group, (xix) a $C_{1-6}$ alkylsulfinyl group, (xx) a $C_{6-10}$ arylsulfinyl group, (xxi) a $C_{1-6}$ alkylsulfonyl group, (xxii) a $C_{6-10}$ arylsulfonyl group, (xxiii) amino, (xxiv) a $C_{1-6}$ acylamino group, (xxv) a mono- or di-$C_{1-6}$ alkylamino group which may optionally be substituted with $C_{6-14}$ aryl, (xxvi) a $C_{3-8}$ cycloalkylamino group, (xxvii) a $C_{6-14}$ arylamino group, (xxviii) a $C_{1-6}$ alkyl-carbonyl group, (xxix) a $C_{1-6}$ alkyl-carbonyloxy group, (xxx) a $C_{6-10}$ aryl-carbonyl group or (xxxi) a 5- or 6-membered heterocyclic group which contains 1 to 4 hetero atoms selected from nitrogen atom, oxygen atom, and sulfur atom besides carbon atom, and which may optionally be substituted with $C_{7-15}$ aralkyl, (3) a $C_{7-15}$ aralkyl group which may optionally be substituted with substituents selected from above-mentioned substituent group A, (4) a $C_{1-15}$ alkyl-carbonyl group, (5) a $C_{1-15}$ alkoxy-carbonyl group, (6) a $C_{6-14}$ aryl-carbonyl group, (7) a $C_{6-14}$ aryl-oxycarbonyl group, (8) a $C_{7-15}$ aralkyl-carbonyl group, (9) a $C_{7-15}$ aralkyl-oxycarbonyl group, (10) carbamoyl which may optionally be substituted with $C_{1-15}$ alkylthio, or (11) a group of the formula —$SO_2$-$R^{23}$, wherein $R^{23}$ is as defined hereinbefore. Still more preferred is (1) hydrogen, (2) a $C_{1-15}$ alkyl group which may optionally be substituted with (i) halogen, (ii) a $C_{1-6}$ alkoxy-carbonyl group, (iii) carbamoyl, (iv) a $C_{1-6}$ alkylamino group which may optionally be substituted with $C_{6-14}$ aryl, or (v) a 5- or 6-membered heterocyclic group which contains 1 to 4 hetero atoms selected from nitrogen atom, oxygen atom, and sulfur atom besides carbon atom, and which may optionally be substituted with $C_{7-15}$ aralkyl, (3) a $C_{7-15}$ aralkyl group which may optionally be substituted with $C_{1-6}$ alkoxy, (4) a $C_{1-15}$ alkyl-carbonyl group, (5) a $C_{6-14}$ aryl-carbonyl group, (6) carbamoyl which may optionally be substituted with $C_{1-15}$ alkylthio, or (7) phenylsulfonyl which may optionally be substituted with $C_{1-6}$ alkyl.

$R^5$ and $R^6$ independently represent hydrogen, an optionally substituted hydrocarbon group, an optionally substituted acyl group, a group of the formula —$NR^{11}R^{12}$, wherein $R^{11}$ and $R^{12}$ are as defined hereinbefore, a group of the formula —$OR^{17}$, wherein $R^{17}$ is as defined hereinbefore, or a group of the formula —$S(O)_nR^{20}$ wherein $R^{20}$ and n are as defined hereinbefore, for instance. Particularly preferred is hydrogen; a $C_{1-15}$ alkyl group, preferably is $C_{1-6}$ alkyl group; a $C_{7-15}$ aralkyl group; a $C_{1-6}$ alkoxy-carbonyl group; a group of the formula —$NR^{112}R^{113}$, wherein $R^{112}$ and $R^{113}$ independently represent hydrogen, a $C_{115}$ alkyl group, a $C_{6-14}$ aryl group, or a $C_{7-15}$ aralkyl group; a group of the formula —$OR^{114}$, wherein $R^{114}$ represents hydrogen, a $C_{1-15}$ alkyl group, a $C_{1-15}$ alkyl-carbonyl group, a $C_{6-14}$ aryl-carbonyl group, or a $C_{7-15}$ aralkyl group; or a group of the formula —$S(O)_nR^{115}$, wherein $R^{115}$ represents a $C_{1-15}$ alkyl group; n has the same meaning as defined hereinbefore.

Especially preferred is hydrogen, a $C_{1-6}$ alkyl group, a $C_{7-20}$ aralkyl group, or a $C_{1-6}$ alkoxy-carbonyl group.

Among them, $R^5$ is preferably hydrogen, a $C_{1-6}$ alkyl group, a $C_{7-20}$ aralkyl group, or a $C_{1-6}$ alkoxy-carbonyl group, and $R^6$ is preferably hydrogen or a $C_{1-6}$ alkyl group.

As the bivalent hydrocarbon group interrupted by one or more hetero atoms as formed by combining $R^1$ and $R^2$, a group of the partial structural formula:

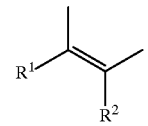

is preferably a group of the formula:

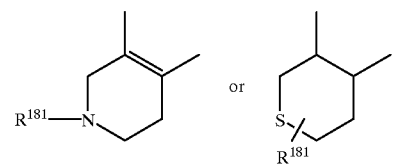

wherein $R^{181}$ represents (1) a $C_{1-15}$ alkyl group which may optionally be substituted with halogen, (2) a $C_{6-14}$ aryl group which may optionally be substituted with, for example, halogen, $C_{1-6}$ alkyl, nitro, hydroxy, or carboxy, or (3) a $C_{1-15}$ alkyl-carbonyl group.

As the alkylene group formed by combining $R^1$ and $R^2$, a group of the partial structural formula:

is preferably a group of the formula:

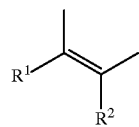

wherein $R^{191}$ represents (1) a $C_{1-15}$ alkyl group which may optionally be substituted with halogen, (2) a $C_{6-14}$ aryl group which may optionally be substituted with halogen, a $C_{1-6}$ alkyl group, nitro, hydroxy, or carboxy, (3) halogen, (4) nitro, (5) hydroxy, (6) carboxy, or (7) a $C_{1-15}$ alkyl-carbonyl group.

W preferably represents oxygen.

When the compound [I] has asymmetric carbon, it may exist as stereoisomers, and the respective isomers and mixtures thereof also fall with in the scope of the present invention. The compound [I] may also exist as stereoisomers when any of its substituent contains asymmetric carbon, and these isomers and mixtures thereof also belongs to the compound [I] of the invention.

When the compound [I] of the present invention has an acidic group, e.g. carboxy, or a basic group, e.g. amino, it can be put to use in the form of a salt, preferably a pharmacologically acceptable salt. The salt, when compound has an acidic group, includes base addition salts such as salts with alkali metals, e.g. sodium, potassium, etc., and salts with alkaline earth metal salts, e.g. calcium, magnesium, etc.. When compound [I] has a basic group, the salt includes acid addition salts such as salts with inorganic acids, e.g. hydrochloric acid, sulfuric acid, phosphoric acid, etc., and salts with organic acids, e.g. acetic acid, propionic acid, citric acid, tartaric acid, malic acid, oxalic acid, methanesulfonic acid, etc.

The compound [I] or a salt thereof according to the present invention can be produced by per se known processes or processes analogous thereto. Specifically the compound of the formula:

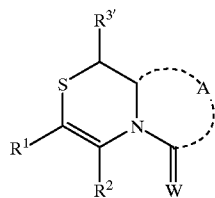

wherein $R^1$, $R^2$, $R^{3'}$, A and W have the same meanings as mentioned above; or a salt thereof can be produced by reacting a compound of the formula:

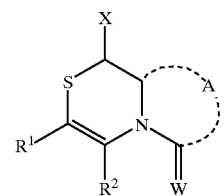

wherein X is an elimination group; $R^1$, $R^2$, W, and A have the same meanings as mentioned above; or a salt thereof with a compound of the formula:

$R^{3'}H$ wherein $R^{3'}$ has the same meaning as mentioned above; or a salt thereof.

Herein above-mentioned compound of the formula:

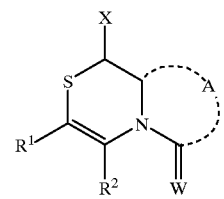

can be obtained by reacting a sulfoxide derivative described in Process 2 mentioned below with a suitable carboxylic acid halide. The reaction conditions may be followed in Process 2.

The compound of the formula:

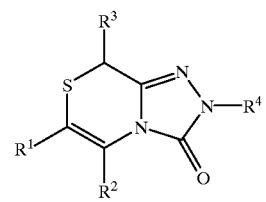

[II]

wherein $R^1$, $R^2$, $R^3$ and $R^4$ have the same meanings as mentioned above; or a salt thereof can be produced by subjecting a compound of the formula:

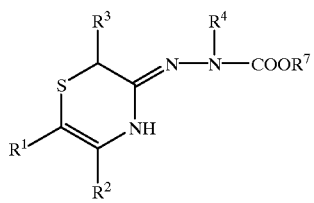

wherein $R^7$ is lower alkyl, preferably $C_{1-6}$ alkyl, $R^1$, $R^2$ and $R^3$ have the same meanings as mentioned above; or a salt thereof to a cyclization reaction.

More specifically, the following processes 1–5 or processes analogous thereto can be utilized.

Compound [II], i.e. compound [I], wherein partial structural formula:

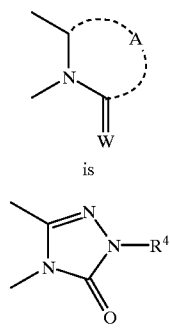

is

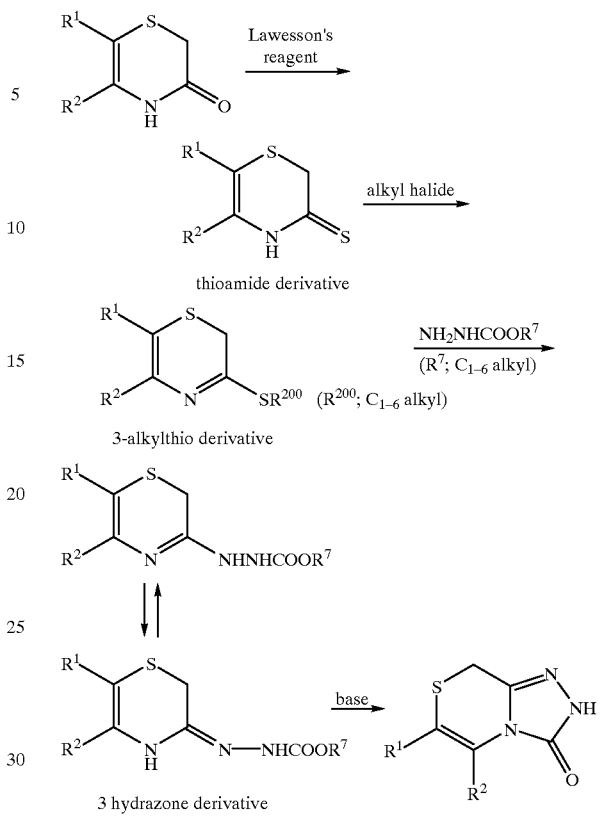

can be produced by the following processes 1–3.

[Process 1: production of compound [II] wherein $R^3=R^4=H$ or a salt thereof]

A monocyclic or condensed 1,4-thiazine derivative obtained by the process (a) described in page 5 of JP-A 275869/1990 is reacted with a sulfurizing agent, e.g. Lawesson's reagent with refluxing under heating to provide the corresponding thioamide derivative. The reaction can be carried out in a suitable solvent, e.g. aromatic hydrocarbons such as toluene, nitrites such as acetonitrile or the like.

This thioamide derivative is reacted with a suitable alkyl halide, e.g. methyl iodide, to provide the 3-alkylthio derivative.

The alkyl halide is used in an equimolar to excess, preferably about 1–3 equivalents, more preferably about 1.5–2 equivalents. The reaction can be preferably carried out in the presence of a suitable base, e.g. an inorganic base such as potassium carbonate. Also this reaction can be carried out in a suitable solvent, e.g. hydrocarbon halides such as dichloromethane, amides such as N,N-dimethylformamide, or the like. The reaction is conducted at room temperature or under heating. The reaction time is about 1–24 hours.

This 3-alkylthio derivative is reacted with a suitable hydrazine derivative, e.g. methyl carbazate to provide a 3-hydrazone derivative. The hydrazine derivative can be used in an equimolar to excess, preferably about 1–3 equivalents and more preferably about 1.5–2 equivalents. This reaction is generally carried out in a solvent not adversely affecting the reaction, e.g. ethers such as tetrahydrofuran or an ethyl ether. Also the reaction is carried out in the presence of a suitable activating agent, e.g. iodine. Furthermore, the reaction temperature is about 10–70° C. The reaction time is 1–12 hours.

The 3-hydrazone derivative is subjected to a cyclization reaction to provide the triazolothiazine derivative of the formula (II) ($R^4=H$). This reaction is carried out in the presence of a suitable base, e.g. pyridine, aqueous solution of potassium hydroxide, or the like. Also the reaction is generally carried out in a solvent not adversely affecting the reaction, e.g. amides such as N,N-dimethylformamide or N,N-dimethylacetamide, alcohols such as methanol or ethanol. The reaction is conducted at about 10–100° C. The reaction time is about 1–12 hours.

Specifically, for example the compound [II] as mentioned above can be produced in accordance with the following reaction scheme.

[Process 2: production of compound [II] wherein $R^3$ is other than hydrogen, or a salt thereof]

The triazolothiazine derivative of the formula (II) ($R^3=H$) is reacted with a suitable peroxide, e.g. m-chloroperbenzoic acid to provide the sulfoxide derivative. The peroxide is used in an equimolar to slight excess, preferably about 1–1.2 equivalents. This reaction is generally carried out in a solvent not adversely affecting the reaction, e.g. hydrocarbon halides such as carbon tetrachloride, dichloromethane, or the like. The reaction is conducted at room temperature or under ice-cooling.

The sulfoxide derivative is reacted with a suitable carboxylic acid halide to provide the oxy-carbonyl derivative (Pummerer rearrangement). The carboxylic acid halide is used in an equivalent to excess, preferably about 1–3 equivalents, and more preferably about 1.5–2 equivalents. This reaction is carried out in a solvent not adversely affecting the reaction, e.g. organic acid such as acetic acid, hydrocarbon halides such as dichloromethane. Also the reaction time is about 1–12 hours. The reaction is carried out under heating.

The oxycarbonyl derivative is reacted with a compound of the formula: $R^{3'}H$, wherein $R^{3'}$ represents a group bonding through a carbon atom, a group bonding through a nitrogen atom, a group bonding through an oxygen atom, or a group bonding through a sulfur atom; e.g. an amine derivative, an alcohol derivative, a thiol derivative, an aromatic homocyclic derivative such as catechol, an aromatic heterocyclic derivative such as furan, an active methylene derivative, or the like, to provide the triazolothiazine derivative of the formula (II) ($R^3=R^{3'}$). The compound of the formula: $R^{3'}H$ is used in an equimolar to excess, preferably about 1–10 equivalents, and more preferably about 1–5 equivalents. The reaction is generally carried out in a solvent not adversely affecting the reaction, e.g. hydrocarbon halides such as 1,2-dichloroethane. The reaction time is about 1–12 hours. The reaction is conducted at room temperature or under heating.

Specifically for example the compound [II] mentioned above can be produced in accordance with the following reaction scheme.

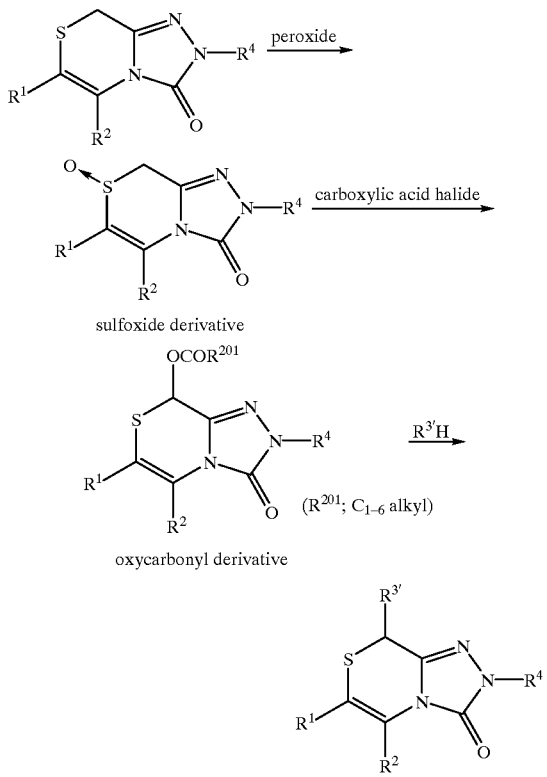

sulfoxide derivative oxycarbonyl derivative

[Process 3: production of compound [II], wherein $R^4$ is other than hydrogen, or a salt thereof]

The triazolothiazine derivative of the formula (II) ($R^4$=H) is reacted with a compound of the formula: $R^{4'}X$, wherein $R^{4'}$ represents a group bonding through a carbon atom or a group bonding through a sulfur atom; X represents a leaving group, e.g. a halide to provide the triazolothiazine derivative of the formula (II) ($R^4$=$R^{4'}$). The reaction scheme is shown below.

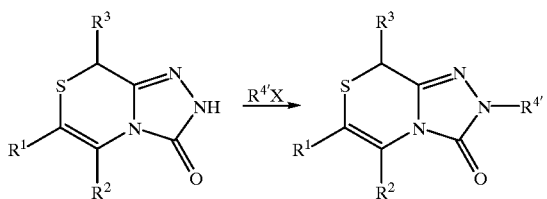

The compound of the formula: $R^{4'}X$ is used in an equimolar to excess, preferably about 1–10 equivalents, and more preferably about 1–5 equivalents. This reaction can be carried out in a solvent not adversely affect the reaction, e.g. amides such as N,N-dimethylformamide, N,N-dimethylacetamide, etc., ketones such as acetone, etc., nitrites such as acetonitrile, etc. Also the reaction is carried out in the presence of a suitable base, e.g. potassium carbonate, sodium hydride, triethylamine, etc. The reaction time is about 1–12 hours. The reaction is conducted at room temperature or under heating.

Compound [III], i.e. the compound [I], wherein the partial structural formula:

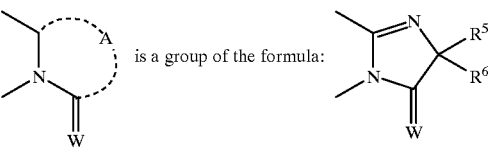

can be produced in accordance with the following processes 4 and 5.

[Process 4: production of compound [III], wherein $R^3$=H or a salt thereof]

A monocyclic or condensed 1,4-thiazine derivative obtained by the process (a) described in page 5 of JP-A 275869/1990 is reacted with an excess of 1,2,4-triazole, nitro-1,2,4-triazole or dinitro-1,2,4-triazole to provide the corresponding triazole substituted derivative. This reaction is carried out in the presence of phosphorus oxychloride and a suitable base, e.g. an amine such as triethylamine. The phosphorus oxychloride is used in an equimolar to slight excess, preferably about 1–1.5 equivalents. This reaction is carried out in a suitable solvent, e.g. an aromatic hydrocarbon such as toluene, a nitrile such as acetonitrile, etc. under reflex. The reaction is carried out for about 1–12 hours. The reaction is carried out under heating.

The triazole substituted derivative is reacted with a suitable amine or amino acid derivative to provide the 3-substituted derivative. The amine or amino acid derivative is used in about 1–3 equivalents. This reaction is carried out in the presence of a suitable base, e.g. inorganic base such as potassium carbonate. Also this reaction is carried out in a suitable solvent, e.g. hydrocarbon halides such as dichloromethane, amides such as N,N-dimethylformamide, etc. The reaction temperature is about 10–70° C. The reaction is carried out for about 1–12 hours.

The 3-substituted derivative is subjected to a cyclization reaction to provide the compound (III) ($R^3$=H). This reaction is carried out in the presence of a suitable base, e.g. pyridine, aqueous solution of potassium hydroxide, or the like. This reaction temperature is about 10–100° C. The reaction is carried out for about 1–12 hours. Also, this reaction is carried out in a solvent not adversely affecting the reaction, e.g. amides such as N,N-dimethylformamide, N,N-dimethylacetamide, etc. or alcohols such as methanol, ethanol, etc.

Specifically for example the compound [III] mentioned above can be produced in accordance with the following reaction scheme.

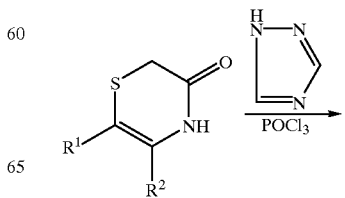

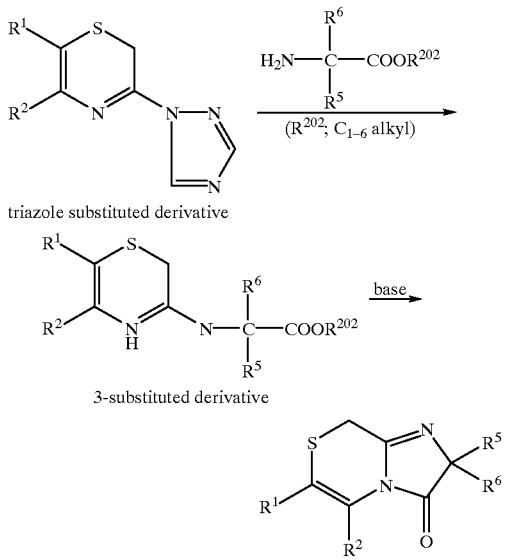

[Process 5: production of compound (III), wherein $R^3$ is other than hydrogen, or a salt thereof]

This compound can be produced by the same procedure as described for process 2 above.

An oxo group of the compound obtained as mentioned above can be easily changed into a thioxo group by the reaction with Lawesson's reagent or $P_2S_5$, etc.

In the above processes 3, the leaving group represented by X may for example be halogen, e.g. chlorine, a $C_{1-6}$ alkyl-carbonyloxy group, or a $C_{6-14}$ aryl-carbonyloxy group, e.g. benzylcarbonyloxy etc.

Other compounds than the above compounds [II] and [III] can also be produced by the above-described processes or processes analogous thereto.

In accordance with the process (a) described in page 5 of JP-A 275869/1990, a starting material can be produced as the monocyclic compound (IV) which can be obtained by using phenathylbromide or a various α-haloketone for the compound (II).

The compound (IV) can be introduced to the starting materials for the present application by the same method described in Working Example 112 of JP-A 275869/1990.

The various compounds described in Table 1–11 shown below can be manufactured by using above starting materials in accordance with the same method mentioned in Working Example 1 in the present application.

The compound [I] or a salt thereof according to the present invention has activity to inhibit splenocyte proliferation response, interleukin-5 production, or/and interferon-gamma production and is useful as an inhibitor of splenocyte proliferation response, interleukin-5 production, and/or interferon-gamma production. Furthermore, the compound [I] or a salt thereof has the property to modulate the functions of T helper-1 cells, (hereinafter referred to sometimes as Th1 cells) and T helper-2 cells (Th2 cells) and, therefore, is useful as a Th1 or Th2 cell function modulator. Particularly it is useful as an inhibitor of the function for Th 2 cell.

Moreover, the compound [I] or a salt thereof is useful as a therapeutic and prophylactic agent for allergic or autoimmune diseases, e.g. rheumatoid arthritis, systemic lupus erythematosus, multiple sclerosis, malignant anemia, ideopathic thrombocytopenic purpura, severe myasthenia, scleroderma, uveitis, Hashimoto's disease, Sjögren's disease, Addison's disease, Basedow's disease, granulocytopenia, bronchial asthma, allergic rhinitis, atopic dermatitis, pollinosis, contact dermatitis, hypersensitivity pneumonitis, lupus nephritis, inflammatory bowel disease, chronic obstructive pulmonary disease, psoriasis, etc.; or as a therapeutic and prophylactic agent for graft rejection and graft-vs-host diseases.

The compound [I] or a salt thereof is of low toxicity and can be used as a safe medicine in human and other warm blooded animals, e.g. mouse, guinea pig, rat, cat, dog, sheep, horse, bovine, or monkey.

For administration of the compound [I] or a salt thereof to a human being, for instance, it can be administered either as it is alone or in the form of a pharmaceutical composition containing a suitable pharmacologically acceptable carrier, excipient, and/or diluent, whether orally or otherwise with assurance of safety.

The pharmaceutical composition mentioned above includes oral dosage forms such as powders, granules, capsules, tablets, etc. and non-oral dosage forms such as injections, drip injections, drug delivery systems for external application, e.g. transnasal, transdermal and other DDSs; and suppositories, e.g. rectal and vaginal suppositories.

Those dosage forms can be manufactured by the per se known pharmaceutical procedures.

Oral dosage forms can be manufactured by adding an excipient, e.g. lactose, sucrose, starch, mannitol, etc.; a disintegrator, e.g. calcium carbonate, carboxymethylcellulose calcium, etc.; a binder, e.g. dextrinized starch, gum arabic, carboxymethylcellulose, polyvinylpyrrolidone, hydroxypropylcellulose, etc.; and/or a lubricant, e.g. talc, magnesium stearate, polyethylene glycol 6000, etc., to compound [I] or a salt thereof and compression-molding the mixture, followed, where necessary, by coating the molding for masking its taste or for the purpose of enteric release or sustained release of the active ingredient. The coating agent that can be used for this purpose includes ethylcellulose, hydroxymethylcellulose, polyoxyethylene glycol, cellulose acetate phthalate, hydroxypropylmethylcellulose phthalate, and Eudragit™ (Rohm, Germany; methacrylic-acrylic acid copolymer).

Injections can be manufactured by dissolving or suspending compound [I] or a salt thereof in an aqueous vehicle together with a dispersant, e.g. Tween 80 (Atlas Powders, U.S.A, HCO60 (Nikko Chemicals), polyethylene glycol, carboxymethylcellulose, sodium alginate, etc.; a preservative, e.g. methyl p-hydroxybenzoate, propyl p-hydroxybenzoate, benzyl alcohol, chlorobutanol, etc.; and an isotonizing agent, e.g. sodium chloride, glycerin, sorbitol, glucose, etc., to provide an aqueous injection or by dissolving or suspending and emulsifying compound [I] or a salt thereof in a vagetable oil such as olive oil, sesame oil, cottonseed oil, or corn oil, propylene glycol, or the like to provide an oily injection.

Dosage forms for external application can be manufactured by processing compound [I] or a salt thereof into a solid, semisolid, or liquid composition. Taking a solid dosage form as an example, it can be manufactured by processing the compound of the invention as it is into powders or in admixture with an excipient, e.g. lactose, mannitol, starch, microcrystalline cellulose, sucrose, etc.; and a thickener, e.g. natural gums, cellulose derivatives, acrylic polymers, etc. A liquid dosage form can be manufactured by processing compound [I] or a salt thereof into an aqueous or oily suspension in substantially the same manner as the manufacture of an injection. A semisolid dosage form is preferably an aqueous or oily gel or ointment. These dosage forms may contain a pH control agent, e.g. carbonic acid, phosphoric acid, citric acid, hydrochloric acid, sodium hydroxide, etc.; an antiseptic, e.g. p-hydroxybenzoic esters, chlorobutanol, benzalkonium chloride, etc.; and other additives.

Suppositories can be manufactured by processing compound [I] or a salt thereof into an oily or aqueous solid, semisolid or liquid suppository form. The oleaginous base that can be used for this purpose includes but is not limited to higher fatty acid glycerides, e.g. caccao butter, Witepsols (Dynamit Nobel), etc.; medium-chain fatty acids, e.g. Mygliols™ (Dynamit Nobel) etc.; and vegetable oils, e.g. sesame oil, soybean oil, cottonseed oil, etc. The aqueous base includes but is not limited to polyethylene glycol and propylene glycol. The aqueous gel base includes but is not limited to natural gums, cellulose derivatives, vinyl polymers, and acrylic polymers.

The dosage of compound [I] or a salt thereof for use in humans may vary with the type and severity of the disease to be treated, the patient's age and other factors, for instance. However, for oral administration, usually about 1 mg to 1 g/day per adult human (body weight: 50 kg), as the active substance, particularly about 4 mg to 200 mg on the same basis, is used advantageously in the treatment of the disease. This daily dosage can be administered in 1–3 divided doses daily.

For parenteral administration of compound [I] or a salt thereof in the form of an injection by the subcutaneous, intravenous, or intramuscular route, the dosage is about 0.5 mg to 200 mg, preferably 1 mg to 50 mg, per day per adult human.

In using the compound [I] or a salt thereof in any of the above-mentioned dosage forms, the known antiinflammatory agent, e.g. steroidal antiinflammatory agent, nonsteroidal antiinflammatory agent, antihistaminic, etc.; and/or immunomodulator, e.g. graft rejection inhibitor, etc., can be included in the formulation.

Specifically, a steroidal antiinflammatory agent such as dexamethasone, hydrocortisone, prednisolone, etc., a nonsteroidal antiinflammatory agent such as aspirin, indomethacin, naphazoline, salbutamol, etc., an antihistaminic such as chlorpheniramine maleate, mequitazine, terfenazine, ketotifen fumarate, oxatomide, tranilast, etc., and/or an immunomodulator such as cyclosporins, tacrolimus, rapamycin, mycophenolic acid, deoxyspergualin, etc. can be formulated.

EXAMPLE

The following Reference Examples, Examples, and Test Examples are intended to describe the present invention merely in further detail and should by no means be construed as defining the scope of the invention.

The $^1$H-NMR spectrum was recorded with Varian GEMINI200 (200 MHz) spectrometer, Japan Electronics JEOL LAMBDA300 (300 MHz) spectrometer, or Brucker AM500 (500 MHz) spectrometer using tetramethylsilane as the internal standard and all δ values were expressed in ppm.

The symbols used in this specification have the following meanings.

s: singlet, d: doublet, t: triplet, dt: double triplet, m: multiplet, br: broad.

Example 1
Production of 5-phenyl-8H-[1,2,4]triazolo-[3,4-c][1,4] thiazin-3(2H)-one (compound 1 in Table 1)

The compound described in Example 112 of JP-A 275869/1990 (5.0 g, 19 mmol) was dissolved in methanol (200 ml), followed by addition of 1.6N potassium hydroxide/H$_2$O (50 ml), and the mixture was stirred at room temperature for 30 minutes. This reaction mixture was concentrated to half its volume and the residue was neutralized with 1N-HCl and extracted with ethyl acetate (300 ml). The extract was washed with water and dehydrated and the solvent was then distilled off under reduced pressure. The resulting light-yellow solid (2.5 g) was recrystallized from methanol-ethyl acetate to provide colorless powdery crystals (2.2 g, 50%).
m.p. 226–228° C.
Elemental analysis, for $C_{11}H_9N_3OS$ C(%) H(%) N(%)
Calcd.: 57.12; 3.92; 18.17
Found : 57.06; 4.00; 17.87
$^1$H-NMR (200 MHz, d$_6$-DMSO)δ: 3.88 (2H, s), 6.38 (1H, s), 7.38 (5H, s), 11.87 (1H, br s).

Example 2

In the same manner as described in JP-A 275869/1990 at line 29, page 8 through line 23, page 9, the 3-methylthio derivative was synthesized from the 1,4-thiazin-3(2H)-one derivative and the reaction product was further reacted with methyl carbazate to give the hydrazone derivative. Then, the procedure described in Example 1 was repeated to provide compounds 2–15 in Table 1, using a suitable base, such as pyridine, in lieu of the aqueous solution of potassium hydroxide where necessary.

Example 3
Production of 5-phenyl-2-methyl-8H-[1,2,4]triazolo[3,4-c] [1,4]thiazin-3(2H)-one (compound 16 in Table 1)

Compound 1 (0.6 g, 2.6 mmol) obtained in Example 1 was dissolved in acetonitrile (30 ml) followed by addition of methyl iodide (1.84 g, 5 equivalents) and potassium carbonate (1.08 g, 3 equivalents), and the mixture was stirred at room temperature for 24 hours. This reaction mixture was concentrated to half its volume and the residue was partitioned between ethyl acetate (200 ml) and water (200 ml). The aqueous layer was re-extracted with ethyl acetate (50 ml) and the two extracts were combined. The organic layer was washed with water and dehydrated and the solvent was distilled off under reduced pressure. The light-yellow solid residue (2.5 g) was crystallized using ethyl acetate-isopropyl ether and recrystallized from chloroform to provide colorless powdery crystals (0.41 g, 64%).
m.p. 127–128° C.
Elemental analysis, for $C_{12}H_{11}N_3OS$ C(%) H(%) N(%)
Calcd.: 58.76; 4.52; 17.13
Found : 58.63; 4.53; 16.86
$^1$H-NMR (200 MHz, d$_6$-DMSO) δ: 3.31 (3H, s), 3.93 (2H, s), 6.47 (1H, s), 7.36 (5H, s like).

Example 4

Starting with the compounds 1–3, 12, 13, 86 or 116 in Table 1–4 described in Example 2, the procedure of Example 3 was repeated to provide compounds 17–29, 96–98, 111, 113 and 117 in Table 1–4 using various halides in lieu of methyl iodide.

Example 5
Production of 5-phenyl-2-methyl-3-oxo-2H,8H-[1,2,4] triazolo[3,4-c][1,4]thiazine-7-oxide (compound 30 in Table 1)

Compound 16 obtained in Example 3 (10.5 g, 43 mmol) was dissolved in dichloromethane (200 ml) and, on an ice bath, a solution of m-chloroperbenzoic acid (9.3 g, 1.25 equivalents) in dichloromethane (400 ml) was added dropwise. After completion of dropwise addition, the mixture was stirred at room temperature for 1 hour. This reaction mixture was serially washed with saturated aqueous solution of sodium hydrogen carbonate and water and dried and the solvent was then distilled off to provide yellow powdery crystals (10.5 g; 94%).

Example 6

Starting with compound 1, compounds 17–29, 96–98, 105, 108, 111, 113 or 117 in Table 1–4 as obtained in Examples 1 and 4, the procedure described in Example 5 was otherwise repeated to provide compounds 31–41, 99–101, 106, 109, 112, 114 and 118 in Table 1–4.

Example 7
Production of 8-acetoxy-5-phenyl-2-methyl-8H-[1,2,4]triazolo[3,4-c][1,4]thiazin-3(2H)-one (compound 42 in Table 2)

Compound 30 in Table 1 obtained in Example 5 (1.0 g, 3.8 mmol) was dissolved in acetic acid (30 ml) and the solution was stirred under heating at 100° C. for 14 hours and further, for ripening, at 130° C. for 3 hours. After cooling, the solvent was distilled off under reduced pressure and the residue was partitioned between dichloromethane (100 ml) and water (100 ml). The aqueous layer was reextracted with dichloromethane (50 ml) and the two extracts were combined. The organic layer was washed with water and dried and the solvent was then distilled off under reduced pressure. The residual red oil (1.4 g) was purified by silica gel column chromatography to provide a colorless amorphous solid (0.53 g, 46%).
$^1$H-NMR (200 MHz, d$_6$-DMSO) δ: 2.10 (3H, s), 3.48 (3H, s), 5.97 (1H, d, J=2 Hz), 6.80 (1H, d, J=2 Hz), 7.43 (SH, s).

Example 8

Starting with compounds 31–41, 99–101, 106, 109, 112, 114 or 118 in Table 1–4 obtained in Example 6, the procedure of Example 7 was otherwise repeated to provide compounds 43–46 in Table 2.

Example 9
Production of 8-(2,3-dihydroxyphenyl)-5-phenyl-2-methyl-8H-[1,2,4]triazolo[3,4-c][1,4]thiazin-3(2H)-one (compound 47 in Table 2)

Compound 42 obtained in Example 7 (1.5 g, 5.0 mmol) was dissolved in 1,2-dichloroethane (50 ml) followed by addition of pyrocatechol (2.73 g, 5 equivalents), and the mixture was refluxed at 120° C. for 24 hours. After cooling, the solvent was distilled off under reduced pressure and the residue was partitioned between dichloromethane (50 ml) and water (100 ml). The aqueous layer was reextracted with dichloromethane (50 ml) and the two extracts were combined. The organic layer was washed with water and dried and the solvent was then distilled off under reduced pressure. The solid residue was purified by silica gel column chromatography to provide colorless crystals (0.25 g). This crystal crop was recrystallized from ethyl acetate-ethyl ether to provide colorless powdery crystals (0.15 g, 9%).
m.p. 200–201° C.
Elemental analysis, for C$_{18}$H$_{15}$N$_3$OS C(%) H(%) N(%)
Calcd.: 61.18; 4.28; 11.89
Found : 61.21; 4.69; 11.64
$^1$H-NMR (200 MHz, d$_6$-DMSO) δ: 3.35 (3H, s), 5.47 (1H, s), 6.41 (1H, s), 6.50 (1H, dd, J=1 Hz, J'=8 Hz), 6.58 (1H, t, J=8 Hz), 6.76 (1H, dd, J=1 Hz, J'=8 Hz), 7.37 (3H, m), 7.47 (2H, m), 9.06 (1H, br s), 9.60 (1H, br s).

Example 10

Starting with compounds 42–46, 81, 102–104, 107, 110 or 115 in Table 1–4 obtained in Example 7, the procedure of Example 9 was repeated using various nucleophilic reagents in lieu of pyrocatechol to provide compounds 47–79, 82–85, and 87–93 in Table 1–4.

The compounds obtained in the above Examples 1–10 and the compounds obtained in similar manners are listed in Tables 1–11.

TABLE 1

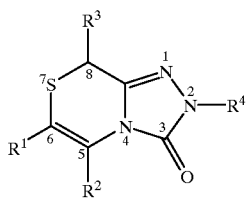

| No. | R$^1$ | R$^2$ | R$^3$ | R$^4$ | yield % | m.p. (° C.) |
|---|---|---|---|---|---|---|
| 1 | H | phenyl | H | H | 50 | 226–228 |
| 2 | H | ethoxycarbonyl | H | H | 86 | amorphous |
| 3 | H | propyl | H | H | 69 | 67–68 |
| 4 | H | 4-cyclohexylphenyl | H | H | | |
| 5 | H | 4-bromophenyl | H | H | 63 | 270–271 |
| 6 | H | methyl | H | H | | |
| 7 | H | 4-methoxyphenyl | H | H | 68 | 204–205 |
| 8 | H | 3,4-dihydroxyphenyl | H | H | | |
| 9 | H | 4-biphenylyl | H | H | | |
| 10 | H | 2-phenoxyphenyl | H | H | | |
| 11 | H | 2-(3-methylbenzofuranyl) | H | H | | |
| 12 | methyl | phenyl | H | H | 86 | 223–224 |
| 13 | methyl | 4-cyclohexylphenyl | H | H | 54 | 211–212 |
| 14 | phenyl | phenyl | H | H | | |
| 15 | 4-methoxyphenyl | methyl | H | H | | |
| 16 | H | phenyl | H | methyl | 64 | 127–128 |
| 17 | H | phenyl | H | butyl | 80 | amorphous |

TABLE 1-continued

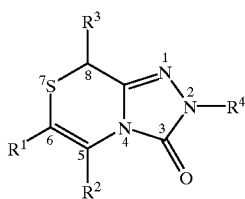

| No. | R¹ | R² | R³ | R⁴ | yield % | m.p. (° C.) |
|---|---|---|---|---|---|---|
| 18 | H | phenyl | H | octyl | 67 | amorphous |
| 19 | H | propyl | H | dodecyl | 85 | amorphous |
| 20 | H | propyl | H | 2-chloroethyl | 83 | amorphous |
| 21 | H | propyl | H | ethoxycarbonylmethyl | 90 | amorphous |
| 22 | H | phenyl | H | acetyl | 68 | 171–173 |
| 23 | H | phenyl | H | benzoyl | 100 | amorphous |
| 24 | H | phenyl | H | carbamoylmethyl | 67 | 194–195 |
| 25 | H | phenyl | H | N-methylthiocarbamoyl | 33 | 203–205 |
| 26 | H | ethoxycarbonyl | H | methyl | 87 | amorphous |
| 27 | H | ethoxycarbonyl | H | 2-chloroethyl | 54 | amorphous |
| 28 | H | propyl | H | 2-methoxybenzyl | 75 | amorphous |
| 29 | methyl | phenyl | H | methyl | 80 | amorphous |
| 30* | H | phenyl | H | methyl | 94 | amorphous |
| 31* | H | phenyl | H | butyl | 95 | amorphous |
| 32* | H | phenyl | H | octyl | 90 | amorphous |
| 33* | H | propyl | H | dodecyl | 95 | amorphous |

TABLE 2

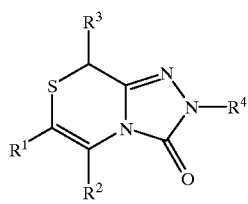

| No. | R¹ | R² | R³ | R⁴ | yield % | m.p. (° C.) |
|---|---|---|---|---|---|---|
| 34* | H | propyl | H | 2-chloroethyl | 90 | amorphous |
| 35* | H | propyl | H | ethoxycarbonyl-methyl | 90 | amorphous |
| 36* | H | phenyl | H | acetyl | 85 | amorphous |
| 37* | H | ethoyxcarbonyl | H | methyl | 90 | amorphous |
| 38* | H | ethoxycarbonyl | H | 2-chloroethyl | 90 | amorphous |
| 39* | H | propyl | H | 2-methoxybenzyl | 93 | amorphous |
| 40* | methyl | phenyl | H | methyl | 91 | amorphous |
| 41* | H | phenyl | H | H | 93 | 268–269 |
| 42 | H | phenyl | acetoxy | methyl | 46 | amorphous |
| 43 | H | phenyl | acetoxy | acetyl | 85 | amorphous |
| 44 | H | phenyl | acetoxy | butyl | 100 | amorphous |
| 45 | H | ethoxycarbonyl | acetoxy | 2-chloroethyl | 90 | amorphous |
| 46 | H | propyl | acetoxy | 2-chloroethyl | 88 | amorphous |
| 47 | H | phenyl | 2,3-dihydroxyphenyl | methyl | 9 | 200–201 |
| 48 | H | phenyl | amino | methyl | 19 | 179–181 |
| 49 | H | phenyl | aminomethyl | methyl | 75 | 170–171 |
| 50 | H | phenyl | methoxy | methyl | 56 | 142–143 |
| 51 | H | phenyl | anilino | methyl | 50 | 243–245 |
| 52 | H | phenyl | 2,3-dihydroxyphenyl | acetyl | 22 | amorphous |
| 53 | H | phenyl | 2 3-diacetoxyphenyl | acetyl | 14 | 241–243 |
| 54 | H | phenyl | 2 3-diacetoxyphenyl | tosyl | 92 | 154–156 |
| 55 | H | ethoxycarbonyl | 2,3-dihydroxyphenyl | acetyl | | |
| 56 | H | phenyl | 2,3-dihydroxyphenyl | o-methoxybenzyl | 11 | 247–249 |
| 57 | H | phenyl | 2,3-dimethoxyphenyl | tosyl | 25 | amorphous |
| 58 | H | phenyl | 2,4-dihydroxyphenyl | methyl | 47 | 271–273 |
| 59 | H | phenyl | 2,5-dihydroxyphenyl | methyl | 48 | 245–246 |
| 60 | H | phenyl | 2-bromophenoxy | tosyl | 12 | 132–134 |
| 61 | H | phenyl | 2-hydroxy-3-methoxy | methyl | 66 | 224–225 |

TABLE 2-continued

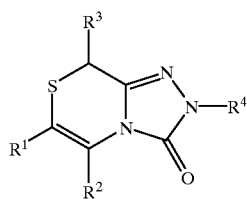

| No. | R¹ | R² | R³ | R⁴ | yield % | m.p. (° C.) |
|---|---|---|---|---|---|---|
| 62 | methyl | 4-cyclohexylphenyl | phenyl 2-hydroxyphenyl | 2-chloroethyl | 70 | 213–214 |
| 63 | H | phenyl | 2-hydroxyphenyl | methyl | 38 | >300 |
| 64 | H | phenyl | 2-hydroxyphenyl | 2-methoxybenzyl | 29 | 242–243 |
| 65 | H | phenyl | 2-hydroxyphenyl | tosyl | 16 | 241–242 |
| 66 | methoxycarbonylmethyl | phenyl | 2-hydroxyphenyl | tosyl | 11 | 102–104 |

TABLE 3

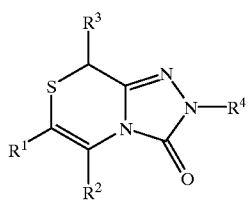

| No. | R¹ | R² | R³ | R⁴ | yield % | m.p. (° C.) |
|---|---|---|---|---|---|---|
| 67 | H | propyl | 2-hydroxyphenoxy | 2-methoxybenzyl | | |
| 68 | H | phenyl | 2-hydroxyethoxy | tosyl | 36 | 205–206 |
| 69 | methyl | 4-cyclohexylphenyl | 2-methoxyphenyl | 2-chloroethyl | 70 | 78–80 |
| 70 | methyl | 4-cyclohexylphenyl | 2-methoxyphenyl | 3-phenylpropylaminoethyl | 71 | 110–113 |
| 71 | H | phenyl | 2-pyridon-1-yl | tosyl | 48 | 243–244 |
| 72 | H | phenyl | 2-pyridylthio | tosyl | 18 | 83–85 |
| 73 | H | phenyl | 3,4-dihydroxyphenyl | methyl | 41 | 225–226 |
| 74 | H | propyl | 3,4-dihydroxyphenyl | methyl | 43 | 193–194 |
| 75 | H | phenyl | 3,4-methylenedioxyphenyl | methyl | 28 | 171–172 |
| 76 | H | phenyl | 3-bromo-4-hydroxyphenyl | tosyl | 35 | 243–245 |
| 77 | H | phenyl | 4-fluorophenoxy | tosyl | 13 | 79–80 |
| 78 | H | phenyl | 4-hydroxyphenyl | tosyl | 35 | 210–211 |
| 79 | H | phenyl | 5-fluoro-2-hydroxyphenyl | tosyl | 38 | 229–231 |
| 80 | H | 4-benzyloxyphenyl | acetoxy | 2-chloroethyl | 54 | 161–162 |
| 81 | methyl | 4-cyclohexylphenyl | acetoxy | 2-chloroethyl | 87 | amorphous |
| 82 | H | phenyl | cyclohexyloxy | tosyl | 53 | 170–171 |
| 83 | H | phenyl | 2,3-dihydroxyphenyl | tosyl | 33 | 235–240 |
| 84 | H | propyl | 2,3-dihydroxyphenyl | methyl | 13 | 213–214 |
| 85 | H | phenyl | phenoxy | methyl | 32 | amorphous |
| 86 | methoxycarbonylmethyl | phenyl | H | H | 51 | 163–164 |
| 87 | H | phenyl | phenylthio | tosyl | 63 | 158–160 |
| 88 | H | phenyl | 2-hydroxynaphthalene-1-yl | tosyl | 56 | 299–300 |
| 89 | H | phenyl | 2-naphthoxy | tosyl | 20 | 170–171 |
| 90 | H | phenyl | 1-hydroxynaphthalene-2-yl | tosyl | 37 | 221–222 |
| 91 | H | phenyl | 1-hydroxynaphthalene-4-yl | tosyl | 10 | 212–213 |
| 92 | H | phenyl | pentafluorophenoxy | tosyl | 44 | 180–181 |

TABLE 3-continued

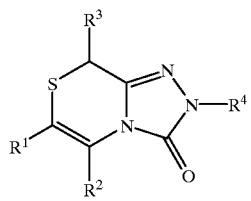

| No. | R¹ | R² | R³ | R⁴ | yield % | m.p. (° C.) |
|---|---|---|---|---|---|---|
| 93 | H | phenyl | 2-pyrrolyl | tosyl | 80 | 234–235 |
| 94 | methoxycarbonyl methyl | phenyl | pentafluoro-phenoxy | tosyl | 21 | 192–193 |
| 95 | methyl | 4-cyclohexylphenyl | 3-propoxy | 2-chloroethyl | 73 | 128–129 |

TABLE 4

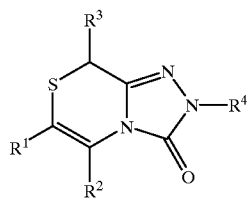

| No. | R¹ | R² | R³ | R⁴ |
|---|---|---|---|---|
| 96 | H | phenyl | H | 2-chloroethyl |
| 97 | H | phenyl | H | tosyl |
| 98 | H | phenyl | H | o-methoxybenzyl |
| 99* | H | phenyl | H | 2-chloroethyl |
| 100* | H | phenyl | H | tosyl |
| 101* | H | phenyl | H | o-methoxybenzyl |
| 102 | H | phenyl | acetoxy | 2-chloroethyl |
| 103 | H | phenyl | acetoxy | tosyl |
| 104 | H | phenyl | acetoxy | o-methoxybenzyl |
| 105 | H | propyl | H | methyl |
| 106* | H | propyl | H | methyl |
| 107 | H | propyl | acetoxy | methyl |
| 108 | H | ethoxycarbonyl | H | acetyl |
| 109* | H | ethoxycarbonyl | H | acetyl |
| 110 | H | ethoxycarbonyl | acetoxy | acetyl |
| 111 | methyl | 4-cyclohexylphenyl | H | 2-chloroethyl |
| 112* | methyl | 4-cyclohexylphenyl | H | 2-chloroethyl |
| 113 | methoxy-carbonyl methyl | phenyl | H | tosyl |

TABLE 4-continued

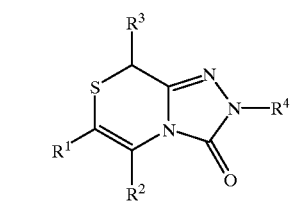

| No. | R¹ | R² | R³ | R⁴ |
|---|---|---|---|---|
| 114* | methoxy-carbonyl methyl | phenyl | H | tosyl |
| 115 | methoxy-carbonyl methyl | phenyl | acetoxy | tosyl |
| 116 | H | 4-benzyloxyphenyl | H | H |
| 117 | H | 4-benzyloxyphenyl | H | 2-chloroethyl |
| 118* | H | 4-benzyloxyphenyl | H | 2-chloroethyl |

*The 7-position of 1,4-thiazine ring is S→0.

TABLE 5

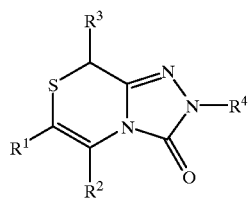

| No. | R¹ | R² | R³ | R⁴ | yield % | m.p. (° C.) |
|---|---|---|---|---|---|---|
| 1) | H | phenyl | H | H | | |
| 2) | H | ethoxycarbonyl | H | H | | |

TABLE 5-continued

| No. | R¹ | R² | R³ | R⁴ | yield % | m.p. (° C.) |
|---|---|---|---|---|---|---|
| 3) | H | propyl | H | H | 44 | 142–145 |
| 4) | H | 4-cyclohexylphenyl | H | H | | |
| 5) | H | 4-bromophenyl | H | H | | |
| 6) | H | methyl | H | H | | |
| 7) | H | 4-methoxyphenyl | H | H | | |
| 8) | H | 3,4-dihydroxyphenyl | H | H | | |
| 9) | H | 4-biphenylyl | H | H | | |
| 10) | H | 2-phenoxyphenyl | H | H | | |
| 11) | H | 2-(3-methylbenzofuran) | H | H | | |
| 12) | methyl | phenyl | H | H | | |
| 13) | methyl | 4-cyclohexylphenyl | H | H | | |
| 14) | phenyl | phenyl | H | H | | |
| 15) | 4-methoxyphenyl | methyl | H | H | | |
| 16) | H | phenyl | H | methyl | | |
| 17) | H | phenyl | H | butyl | | |
| 18) | H | phenyl | H | octyl | | |
| 19) | H | propyl | H | dodecyl | | |
| 20) | H | propyl | H | 2-chloroethyl | | |
| 21) | H | propyl | H | ethoxycarbonylmethyl | | |
| 22) | H | phenyl | H | acetyl | | |
| 23) | H | phenyl | H | benzoyl | | |
| 24) | H | phenyl | H | carbamoylmethyl | | |
| 25) | H | phenyl | H | N-methylthiocarbamoyl | | |
| 26) | H | ethoxycarbonyl | H | methyl | | |
| 27) | H | ethoxycarbonyl | H | 2-chloroethyl | | |
| 28) | H | propyl | H | 2-methoxybenzyl | | |
| 29) | methyl | phenyl | H | methyl | | |
| 30) | H | phenyl | H | methyl | | |
| 31) | H | phenyl | H | butyl | | |
| 32) | H | phenyl | H | octyl | | |
| 33) | H | propyl | H | dodecyl | | |
| 34) | H | propyl | H | 2-chloroethyl | | |
| 35) | H | propyl | H | ethoxycarbonyl-methyl | | |

TABLE 6

| No. | R¹ | R² | R³ | R⁴ |
|---|---|---|---|---|
| 36) | H | phenyl | H | acetyl |
| 37) | H | ethoxycarbonyl | H | methyl |
| 38) | H | ethoxycarbonyl | H | 2-chloroethyl |
| 39) | H | propyl | H | 2-methoxybenzyl |
| 40) | methyl | phenyl | H | methyl |
| 41) | H | phenyl | H | H |
| 42) | H | phenyl | acetoxy | methyl |
| 43) | H | phenyl | acetoxy | acetyl |
| 44) | H | phenyl | acetoxy | butyl |
| 45) | H | ethoxycarbonyl | acetoxy | 2-chloroethyl |
| 46) | H | propyl | acetoxy | 2-chloroethyl |

TABLE 6-continued

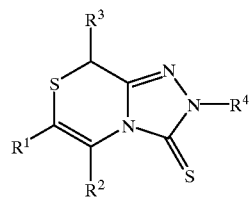

| No. | R¹ | R² | R³ | R⁴ |
|---|---|---|---|---|
| 47) | H | phenyl | 2,3-dihydroxyphenyl | methyl |
| 48) | H | phenyl | amino | methyl |
| 49) | H | phenyl | aminomethyl | methyl |
| 50) | H | phenyl | methoxy | methyl |
| 51) | H | phenyl | anilino | methyl |
| 52) | H | phenyl | 2,3-dihydroxyphenyl | acetyl |
| 53) | H | 4-(4-biphenylyl)oxyphenyl | H | 2-chloroethyl |
| 54) | H | 4-(4-biphenylyl)oxyphenyl | H | 3-phenylpropylaminoethyl |
| 55) | H | 4-(4-biphenylyl)oxyphenyl | H | 3,3-diphenylpropylaminoethyl |
| 56) | H | 4-(4-pyridylmethyl)oxyphenyl | H | 2-chloroethyl |
| 57) | H | 4-(4-pyridylmethyl)oxyphenyl | H | 3-phenylpropylaminoethyl |
| 58) | H | 4-(3-phenylpropylaminocarbonylmethoxyphenyl) | H | 2-chloroethyl |
| 59) | H | 4-(3-phenylpropylaminocarbonylmethoxyphenyl) | H | 3-phenylpropylaminoethyl |
| 60) | H | 4-benzyloxyphenyl | H | 2-chloroethyl |
| 61) | H | 4-benzyloxyphenyl | H | 3-phenylpropylaminoethyl |
| 62) | H | 4-bromophenyl | H | 3,3-diphenylpropylaminoethyl |
| 63) | H | 4-bromophenyl | H | 4,4-diphenylbutylaminoethyl |
| 64) | methyl | 4-cyclohexylphenyl | H | 3-phenylpropylaminoethyl |

TABLE 7

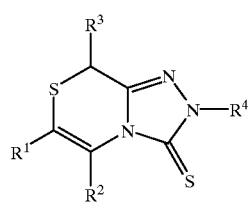

| No. | R¹ | R² | R³ | R⁴ |
|---|---|---|---|---|
| 65) | methyl | 4-cyclohexylphenyl | H | propylaminoethyl |
| 66) | methyl | 4-cyclohexylphenyl | H | 3,3-diphenylpropylaminoethyl |
| 67) | H | 4-methoxyphenyl | H | 3,3-diphenylpropylaminoethyl |
| 68) | H | 4-biphenylyl | H | 3-phenylpropylaminoethyl |
| 69) | H | 4-t-butylphenyl | H | 3,3-diphenylpropylaminoethyl |
| 70) | H | phenyl | H | 2-(1-benzylpiperazin-4-yl)ethyl |
| 71) | methoxycarbonylmethyl | phenyl | pentafluorophenyl | tosyl |

TABLE 7-continued

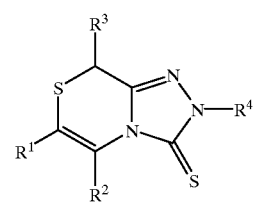

| No. | R¹ | R² | R³ | R⁴ |
|---|---|---|---|---|
| 72) | H | phenyl | pentafluorophenyl | tosyl |
| 73) | H | phenyl | phenoxy | methyl |
| 74) | H | 4-benzyloxyphenyl | phenylthio | 2-chloroethyl |
| 75) | methyl | 4-cyclohexylphenyl | phenylthio | 2-chloroethyl |
| 76) | H | phenyl | phenylthio | tosyl |
| 77) | methyl | 4-cyclohexylphenyl | propoxy | 2-chloroethyl |
| 78) | H | phenyl | propoxy | tosyl |
| 79) | H | phenyl | 2-pyrrolyl | tosyl |

TABLE 8

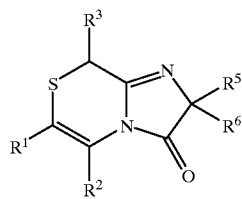

| No. | R¹ | R² | R³ | R⁵ | R⁶ |
|---|---|---|---|---|---|
| (1) | H | phenyl | H | H | H |
| (2) | H | ethoxycarbonyl | H | H | H |
| (3) | H | propyl | H | H | H |
| (4) | H | 4-cyclohexylphenyl | H | H | H |
| (5) | H | 4-bromophenyl | H | H | H |
| (6) | H | methyl | H | H | H |
| (7) | H | 4-methoxyphenyl | H | H | H |
| (8) | H | 3,4-dihydroxyphenyl | H | H | H |
| (9) | H | 4-biphenylyl | H | H | H |
| (10) | H | 2-phenoxyphenyl | H | H | H |
| (11) | H | 2-(3-methylbenzofuran) | H | H | H |
| (12) | methyl | phenyl | H | H | H |
| (13) | methyl | 4-cyclohexylphenyl | H | H | H |
| (14) | phenyl | phenyl | H | H | H |
| (15) | 4-methoxyphenyl | methyl | H | H | H |
| (16) | H | phenyl | H | methyl | H |
| (17) | H | phenyl | H | isobutyl | H |
| (18) | H | phenyl | H | benzyl | H |
| (19) | H | propyl | H | methyl | H |
| (20) | H | propyl | H | isobutyl | H |
| (21) | H | propyl | H | benzyl | H |
| (22) | H | phenyl | H | methyl | methyl |
| (23) | H | phenyl | H | ethoxycarbonylmethyl | H |
| (24) | H | phenyl | H | ethyl | H |
| (25) | H | phenyl | H | propyl | H |
| (26) | H | ethoxycarbonyl | H | methyl | H |
| (27) | H | ethoxycarbonyl | H | isobutyl | H |
| (28) | H | propyl | H | benzyl | H |
| (29) | methyl | phenyl | H | methyl | H |
| (30) | H | phenyl | H | methyl | H |
| (31) | H | phenyl | H | isobutyl | H |
| (32) | H | phenyl | H | benzyl | H |
| (33) | H | propyl | H | methyl | H |

TABLE 9

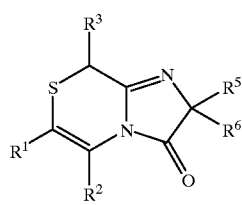

| No. | R¹ | R² | R³ | R⁵ | R⁶ |
|---|---|---|---|---|---|
| (34) | H | propyl | H | isobutyl | H |
| (35) | H | propyl | H | benzyl | H |
| (36) | H | phenyl | H | methyl | methyl |
| (37) | H | ethoxycarbonyl | H | methyl | H |
| (38) | H | ethoxycarbonyl | H | isobutyl | H |
| (39) | H | propyl | H | benzyl | H |
| (40) | methyl | phenyl | H | methyl | H |
| (41) | H | phenyl | H | methoxycarbonylmethyl | H |
| (42) | H | phenyl | acetoxy | H | H |
| (43) | H | phenyl | acetoxy | methyl | H |
| (44) | H | phenyl | acetoxy | isobutyl | H |
| (45) | H | ethoxycarbonyl | acetoxy | methyl | H |

TABLE 9-continued

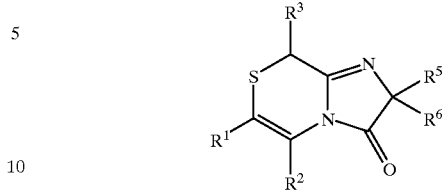

| No. | R¹ | R² | R³ | R⁵ | R⁶ |
|---|---|---|---|---|---|
| (46) | H | propyl | acetoxy | methyl | H |
| (47) | H | phenyl | 2,3-dihydroxyphenyl | methyl | H |
| (48) | H | phenyl | amino | methyl | H |
| (49) | H | phenyl | aminomethyl | methyl | H |
| (50) | H | phenyl | methoxy | methyl | H |
| (51) | H | phenyl | anilino | methyl | H |
| (52) | H | phenyl | 2,3-dihydroxyphenyl | isobutyl | H |

TABLE 10

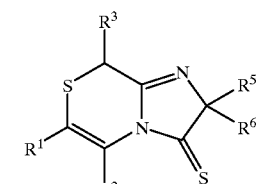

| No. | R¹ | R² | R³ | R⁵ | R⁶ |
|---|---|---|---|---|---|
| [1] | H | phenyl | H | H | H |
| [2] | H | ethoxycarbonyl | H | H | H |
| [3] | H | propyl | H | H | H |
| [4] | H | 4-cyclohexylphenyl | H | H | H |
| [5] | H | 4-bromophenyl | H | H | H |
| [6] | H | methyl | H | H | H |
| [7] | H | 4-methoxyphenyl | H | H | H |
| [8] | H | 3,4-dihydroxyphenyl | H | H | H |
| [9] | H | 4-biphenylyl | H | H | H |
| [10] | H | 2-phenoxyphenyl | H | H | H |
| [11] | H | 2-(3-methylbenzofuran) | H | H | H |
| [12] | methyl | phenyl | H | H | H |
| [13] | methyl | 4-cyclohexylphenyl | H | H | H |
| [14] | phenyl | phenyl | H | H | H |
| [15] | 4-methoxyphenyl | methyl | H | H | H |
| [16] | H | phenyl | H | methyl | H |
| [17] | H | phenyl | H | isobutyl | H |
| [18] | H | phenyl | H | benzyl | H |
| [19] | H | propyl | H | methyl | H |
| [20] | H | propyl | H | isobutyl | H |
| [21] | H | propyl | H | benzyl | H |
| [22] | H | phenyl | H | methyl | methyl |
| [23] | H | phenyl | H | ethoxycarbonylmethyl | H |
| [24] | H | phenyl | H | ethyl | H |
| [25] | H | phenyl | H | propyl | H |
| [26] | H | ethoxycarbonyl | H | methyl | H |
| [27] | H | ethoxycarbonyl | H | isobutyl | H |
| [28] | H | propyl | H | benzyl | H |
| [29] | methyl | phenyl | H | methyl | H |
| [30] | H | phenyl | H | methyl | H |
| [31] | H | phenyl | H | isobutyl | H |
| [32] | H | phenyl | H | benzyl | H |
| [33] | H | propyl | H | methyl | H |

TABLE 11

[structure: condensed 1,4-thiazine derivative with substituents $R^1$, $R^2$, $R^3$, $R^5$, $R^6$ and S]

| No. | $R^1$ | $R^2$ | $R^3$ | $R^5$ | $R^6$ |
|---|---|---|---|---|---|
| [34] | H | propyl | H | isobutyl | H |
| [35] | H | propyl | H | benzyl | H |
| [36] | H | phenyl | H | methyl | methyl |
| [37] | H | ethoxycarbonyl | H | methyl | H |
| [38] | H | ethoxycarbonyl | H | isobutyl | H |
| [39] | H | propyl | H | benzyl | H |
| [40] | methyl | phenyl | H | methyl | H |
| [41] | H | phenyl | H | methoxy-bonylmethyl | H |
| [42] | H | phenyl | acetoxy | H | H |
| [43] | H | phenyl | acetoxy | methyl | H |
| [44] | H | phenyl | acetoxy | isobutyl | H |
| [45] | H | ethoxycarbonyl | acetoxy | methyl | H |
| [46] | H | propyl | acetoxy | methyl | H |
| [47] | H | phenyl | 2,3-dihydroxyphenyl | methyl | H |
| [48] | H | phenyl | amino | methyl | H |
| [49] | H | phenyl | aminomethyl | methyl | H |
| [50] | H | phenyl | methoxy | methyl | H |
| [51] | H | phenyl | anilino | methyl | H |
| [52] | H | phenyl | 2,3-dihydroxyphenyl | isobutyl | H |

The sulfur atom at 7-position in 1,4-thiazine ring for the condensed 1,4-thiazine derivative (I) of the present invention may be oxidized.

In Table 1–4, the sulfur atoms at 7-position in 1,4-thiazine ring for the compounds no. 30–41, 99–101, 106, 109, 112, 114 and 118 which are pointed out by asterisk are oxidized (S→O).

Test Example 1
Inhibitory effect on the ascaris antigen-specific proliferation response of murine splenocytes Using the ascaris antigen known to potently activate T helper-2 cells, BALB/c mice which would show a high level of expression of T helper-2 cell responses were sensitized and the inhibitory activity of compound 47 in Table 2 on the ascaris antigen-specific proliferation response of splenocytes was investigated.

In the first place, BALB/c mice (female, 9 weeks old, Charles River Japan) were intraperitoneally dosed with 40 μg/mouse of ascaris extract (L.S.L, Japan) and, as adjuvant, 0.5 μg/mouse of synthetic TAN-1511 derivative [(2R,6R)-2-amino-6,7-bis(hexadecanoyloxy)-4-thiaheptanoylGly-Gly-Glu 2Na] [The Journal of Antibiotics, 48, 589–603 (1995)] and splenocytes were harvested from the spleens after 14 days. Then, 50 μg/ml of ascaris extract was added to RPMI1640 medium (Bio-Wittaker Inc., U.S.A.) containing $3 \times 10^6$/ml splenocytes obtained above, 2 mM L-glutamine, 20 μg/ml gentamicin (Bio-Wittaker Inc., U.S.A.), and 10% fetal calf serum (Bio-Wittaker Inc., U.S.A.), and after addition of compound 47 at a varying concentration, the mixture was incubated under 5% $CO_2$ at 37° C. for 3 days. The proliferation of splenocytes was quantitated by the MTT reduction method [Tada et al., Journal of Immunological Methods, 93, 157, 1986]. The results are presented in Table 12.

TABLE 12

| Concentration of Compound 47 (μM) | Proliferation rate[1] |
|---|---|
| 1.25 | 0.14 |
| 0.625 | 0.24 |
| 0.313 | 0.27 |

[1] The proliferation of splenocytes in the compound-free group is taken as 1.

It will be apparent from Table 12 that compound 47 according to the present invention exhibits a remarkable inhibitory action on the ascaris antigen-specific proliferation response of murine splenocytes.

Test Example 2
Inhibitory effect on interleukin-5 production

Splenocytes were co-incubated with compound 47 in Table 2 under the same conditions as in Test Example 1 for 4 days and interleukin-5 (briefly, IL-5) in the culture supernatant was assayed by ELISA (a commercial kit available from Endogen, U.S.A.). The results are presented in Table 13.

TABLE 13

| Concentration of Compound 47 (μM) | Production rate[1] |
|---|---|
| 1.25 | 0.15 |
| 0.625 | 0.47 |

[1] The production of IL-5 in the compound-free group is taken as 1.

It will be aparent from Table 13 that compound 47 according to the present invention exhibits remarkable IL-5 production inhibitory activity.

Test Example 3
Inhibitory effect on the PPD-specific proliferation response of murine splenocytes Using the PPD known to potently activate T helper-1 cells, $C_{57}BL/6$ mice which would show a high level of expression of T helper-1 cell responses were sensitized and the inhibitory activity of compound 47 in Table 2 on the PPD-specific proliferation response of splenocytes was investigated.

In the first place, $C_{57}BL/6$ mice (male, 9 weeks old, Charles River Japan) were intraperitoneally dosed with 10 μg/mouse of PPD (BCG Japan) and, as adjuvant, 0.5 μg/mouse of synthetic TAN-1511 derivative [(2R,6R)-2-amino-6,7-bis(hexadecanoyloxy)-4-thiaheptanoyl-Gly-Gly-Glu 2Na] and splenocytes were harvested from the spleens after 7 days. Then, 1 μg/ml of PPD was added to RPMI1640 medium (Bio-Wittaker Inc., U.S.A.) containing $3 \times 10^6$/ml splenocytes obtained above, 2 mM L-glutamine, 20 μg/ml gentamicin (Bio-Wittaker Inc., U.S.A.), and 10% fetal calf serum (Bio-Wittaker Inc., U.S.A.), and after addition of compound 47 at a varying concentration, the mixture was incubated under 5% $CO_2$ at 37° C. for 3 days. The proliferation of splenocytes was quantitated by the MTT reduction method as in Test Example 1. The results are presented in Table 14.

47

TABLE 14

| Concentration of Compound 47 (μM) | Proliferation rate[1] |
|---|---|
| 1.25 | 0.58 |
| 0.625 | 0.45 |
| 0.313 | 0.58 |

1) The proliferation of splenocytes in the compound-free group is taken as 1.

It will be apparent from Table 14 that compound 47 according to the present invention exhibits a remarkable inhibitory action on the PPD-specific proliferation response of murine splenocytes.

Test Example 4

Inhibitory effect on interferon-gamma production

Splenocytes were co-incubated with compound 47 under the same conditions as in Test Example 3 for 4 days and interferon-gamma in the culture supernatant was assayed by ELISA (a commercial kit available from Gibco BRL, U.S.A.). The results are presented in Table 15.

TABLE 15

| Concentration of Compound 47 (μM) | Production rate[1] |
|---|---|
| 0.313 | <0.02 |
| 0.156 | 0.12 |

1) The production of interferon-gamma in the compound-free group is taken as 1.

It will be aparent from Table 15 that compound 47 according to the present invention has remarkable interferon-gamma production inhibitory activity.

Compound [I] or a salt thereof of the present invention suppresses the antigen-specific proliferative response of T helper-1 or helper 2 cells and the associated production of major cytokines such as interleukin-5 and interferon-gamma to correct for a derangement of the balance of T cell subsets which is of significance in human immune diseases.

Therefore, compound [I] or a salt thereof of the present invention is useful as a splenocyte proliferative response, interleukin-5 production, or interferon-gamma production inhibitor composition and a T helper-1 or T helper-2 cell function modulator composition, particularly T helper-2 cell function inhibitor composition.

Compound [I] or a salt thereof of the present invention is further useful as a therapeutic and prophylactic agent for allergic or autoimmune diseases, e.g. rheumatoid arthritis, systemic lupus erythematosus, multiple sclerosis, malignant anemia, ideopathic thrombocytopenic purpura, severe myasthenia, scleroderma, uveitis, Hashimoto's disease, Sj ögren's disease, Addison's disease, Basedow's disease, granulocytopenia, bronchial asthma, allergic rhinitis, atopic dermatitis, pollinosis, contact dermatitis, hypersensitivity pneumonitis, lupus nephritis, inflammatory bowel disease, chronic obstructive pulmonary disease, psoriasis, etc.

What is claimed is:

48

1. A compound of the formula:

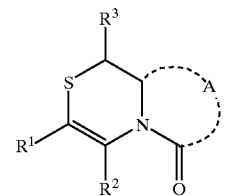

[I]

wherein:
the moiety represented by the partial structural formula:

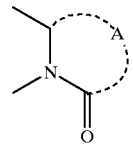

is a group of the formula:

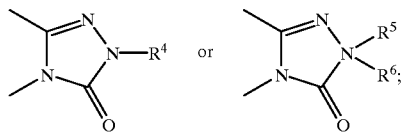

$R^1$ is
(1) a hydrogen atom,
(2) a $C_{1-15}$ alkyl group which is optionally substituted with $C_{1-6}$ alkoxy-carbonyl, or
(3) a $C_{6-14}$ aryl group which is optionally substituted with $C_{1-6}$ alkoxy;

$R^2$ is
(1) a $C_{6-14}$ aryl group which is optionally substituted with (i) a hydroxy group, (ii) a halogen atom, (iii) a $C_{1-15}$ alkyl group, (iv) a $C_{37}$ cycloalkyl group, (v) a $C_{6-14}$ aryl group, (vi) a $C_{6-20}$ aryloxy group, (vii) a $C_{7-20}$ aralkyloxy group or (viii) a $C_{1-6}$ alkoxy group which is optionally substituted with a $C_{7-20}$ aralkylcarbamoyl group, or pyridyl,
(2) a $C_{1-15}$ alkyl group,
(3) a $C_{1-15}$ alkoxy-carbonyl group, or
(4) a benzofuryl which is optionally substituted with $C_{1-15}$ alkyl;

$R^3$ is
(1) a hydrogen atom,
(2) a $C_{1-15}$ alkyl group which is optionally substituted with an amino,
(3) an amino group which is optionally substituted with a $C_{6-14}$ aryl group,
(4) a $C_{6-14}$ aryl group which is optionally substituted with (i) a hydroxy group, (ii) a halogen atom, or (iii) a $C_{1-6}$ alkoxy group,
(5) a group of the formula: —O—$R^{28}$, wherein $R^{28}$ is (i) a $C_{1-15}$ alkyl group which is optionally substituted with a hydroxy group, (ii) a $C_{6-14}$ aryl group which is optionally substituted with a halogen atom or hydroxy group, (iii) a $C_{3-7}$ cycloalkyl group, or (iv) a $C_{1-6}$ alkylcarbonyl group, or
(6) a $C_{6-14}$ arylthio group $R^4$ is
(1) a hydrogen atom,
(2) a $C_{1-15}$ alkyl group which is optionally substituted with (i) a halogen atom, (ii) a $C_{1-6}$ alkoxy-carbonyl group, (iii) a carbamoyl group, (iv) a $C_{1-6}$ alkylamino group which is optionally substituted with $C_{6-14}$ aryl, or (v) a piperazinyl group which is optionally substituted with $C_{7-15}$ aralkyl, (3) a $C_{7-15}$ aralkyl group which is optionally substituted with $C_{1-6}$ alkoxy, (4) a $C_{1-15}$ alkyl-carbonyl group, (5) a $C_{6-14}$ aryl-carbonyl group, (6) a carbamoyl which is optionally substituted with $C_{1-6}$ alkylthio, or (7) a phenylsulfonyl which is optionally substituted with a $C_{1-6}$ alkyl group;

$R^5$ is (1) a hydrogen atom, (2) a $C_{1-6}$ alkyl group, or (3) a $C_{7-20}$ aralkyl group $R^6$ is (1) a hydrogen atom or (2) a $C_{1-6}$ alkyl group;

or a salt thereof.

2. The compound as claimed in claim 1, wherein the compound of the formula is represented by the formula:

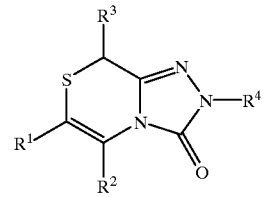

[II]

wherein $R^1, R^2, R^3$ and $R^4$ have the same meanings as defined claim 1.

3. A compound of 8-(2-hydroxyphenyl)-5-phenyl-2-methyl-8H-[1,2,4]triazolo[3,4-c][1,4]thiazin-3(2H)-one or a salt thereof.

4. A compound of 8-(2,3-dihydroxyphenyl)-5-phenyl-2-methyl-8H-[1,2,4]triazolo[3,4-c][1,4]thiazin-3(2H)-one or a salt thereof.

5. A pharmaceutical composition comprising a compound or a salt thereof as claimed in claim 1 and a pharmaceutically acceptable carrier, excipient or diluent.

6. A method for treating or preventing graft rejection or graft-vs-host disease in a mammal, which comprises administering to said mammal an effective amount of a pharmaceutical composition as claimed in claim 5.

* * * * *

UNITED STATES PATENT AND TRADEMARK OFFICE
CERTIFICATE OF CORRECTION

PATENT NO.    : 6,004,954
DATED         : December 21, 1999
INVENTOR(S)   : Shuichi Furuya et al.

It is certified that error appears in the above-identified patent and that said Letters Patent is hereby corrected as shown below:

Column 48
Line 20, the formula

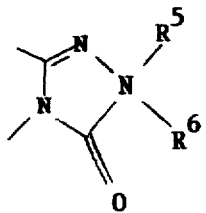

Should read

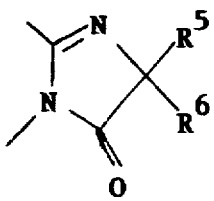

Signed and Sealed this

Twenty-eighth Day of August, 2001

*Attest:*

*Attesting Officer*

NICHOLAS P. GODICI
*Acting Director of the United States Patent and Trademark Office*